(12) United States Patent
Blanche et al.

(10) Patent No.: US 6,649,394 B1
(45) Date of Patent: Nov. 18, 2003

(54) TOPOISOMERASE IV, CORRESPONDING NUCLEOTIDE SEQUENCES AND USES THEREOF

(75) Inventors: Francis Blanche, Paris (FR); Béatrice Cameron, Paris (FR); Joël Crouzet, Sceaux (FR); Alain Famechon, Janville-sur-Juine (FR); Lucia Ferrero, Paris (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 09/398,184

(22) Filed: Sep. 17, 1999

Related U.S. Application Data

(62) Division of application No. 08/776,265, filed on Jan. 24, 1997, now Pat. No. 6,001,631.

(51) Int. Cl.[7] .................................................. C12N 9/90

(52) U.S. Cl. ........................ 435/233; 435/183; 435/194; 530/350; 536/23.1; 536/23.2; 536/23.7

(58) Field of Search ................................. 435/233, 183, 435/194; 530/350, 23.1, 23.2, 23.7

(56) References Cited

U.S. PATENT DOCUMENTS 6,001,631 A * 12/1999 Blanche et al. ............. 435/233

OTHER PUBLICATIONS

Sigma Catalog (1993) p. 484; Catalog No. G7403, Jan. 1993.*

Bagdasarian, M. et al., "Specific–purpose plasmid cloning vectors. II. Broad host range, high copy No., RSF1010–derived vectors, and a host–vector system for gene cloning in *Pseudomonas*," Gene 16:237–247 (1981).

Ferrero et al., "Cloning and primary structure of *Staphylococcus aureus* DNA isomerase IV a primary target of fluoroquinolones," Molecular Microbiology 13(4):641–653 (1994).

Ferrero et al., "Analysis of gyrA and gr1A Mutations in Stepwise–Selected Ciprofloxacin–Resistant Mutants of *Staphylococcus aureus*," Antimicrobial Agents and Chemotherapy 39(7):1554–1558 (1995).

Gellert, M. et al. "DNA gyrase: An enzyme that introduces superhelical turns into DNA," Proc. Natl. Acad. Sci. USA 73:3872–3876 (1976).

Higgins, D.G. and Sharp, P.M., "CLUSTAL: a package for performing multiple sequence alignment on a microcomputer," Gene 73:237–244 (1988).

Holmes, M.L. and Dyall–Smith, M., "Mutations in DNA Gyrase Result in Novobiocin Resistance in Halophilic Archaebacteria," J. Bacteriol. 173(2):642–648 (1991).

Hopewell, R. et al., "DNA Cloning and Organization of the *Staphylococcus aureus* gyrA and gyrB Genes Close Homology among Gyrase Proteins and Implications for 4–Quinolone Action and Resistance," J. Bacteriol., 172(6):3481–3484 (1990).

Hooper, D.C. and Wolfson, J.S., "Mechanisms of Quinolone Action and Bacterial Killing," In Quinolone Antimicrobial Agents, Hooper, D.C., and Wolfson, J.S. (eds), American Society of Microbiology, Washington, D.C., pp. 53–75 (1993).

Horowitz, D.S. and Wang, J.C., "Mapping the Active Site Tyrosine of *Escherichia coli* DNA Gyrase," J. Biol. Chem. 262(11):5339–5344 (1987).

Kato, J. et al., "Purification and Characterization of DNA Topoisomerase IV in *Escherichia coli*," J. Biol. Chem. 267(36):25676–25684 (1992).

Kato, J. et al., "New Topoisomerase Essential for Chromosome Segregation in *E. coli*," Cell 63(2):393–404 (1990).

Luttinger, A.L. et al., "A Cluster of Genes That Affects Nucleoid Segregation in *almonella typhimurium*," New Biol 3:(7)687–697 (1991).

Margerrison, E.E.C. et al., "Nucleotide Sequence of the *Staphyloccus aureus* gyrB–gyrA Locus Encoding the DNA Gyrase A and B Proteins," J. Bacteriol., Am. Soc. Microbiol., 174(5):1596–1603 (1992).

Ng, E. Y. et al., "Novel Mutations in Topoisomerase IV (Topo4) in Quinolone–Resistant (QR) flqA Mutants and Their Interaction with QR gyrA Mutations in *Staphylococcus aureus*," 95th General Meeting of the American Society for Microbiology, Washington, D.C., May 21–25, 1995. Abstracts General Meeting of the American Society for Microbiology 95(0).

Normark, S. et al., "Overlapping Genes," Ann. Rev. Genet. 17:499–525 (1983).

Novick, R.P., "The Staphylococcus as a Molecular Genetic System," in Molecular Biology of the Staphyloccoci, Novick, R.P. (ed). VCH Publishers, Inc., New York, pp. 1–37 (1990).

Peng, H. and Marians, K. J., "*Escherichia coli* Topoisomerase IV," J. Biol. Chem. 268 (32):24481–24490 (1993).

Peng, H. and Marians, K. J., "Decatenation activity of topoisomerase IV during oriC and pBR322 DNA replication in vitro," Proc. Natl. Acad. Sci. 90:8571–8575 (1993).

Sreedharan S. et al., "DNA Gyrase gyrA Mutations in Ciprofloxacin–Resistant Strains of *Staphylococcus aureus* Close Similarity with Quinolone Resistance Mutations in *Escherichia coli*," J. Bacteriol., 172(12):7260–7262 (1990).

(List continued on next page.)

Primary Examiner—Richard Hutson
(74) Attorney, Agent, or Firm—Finnegan, Henderson, Farabow, Garrett & Dunner LLP

(57) ABSTRACT

A novel topoisomerase IV, nucleotide sequences coding for said enzyme, corresponding vectors, and the use of said enzyme for screening biologically active materials.

8 Claims, 5 Drawing Sheets

OTHER PUBLICATIONS

Figure 1:
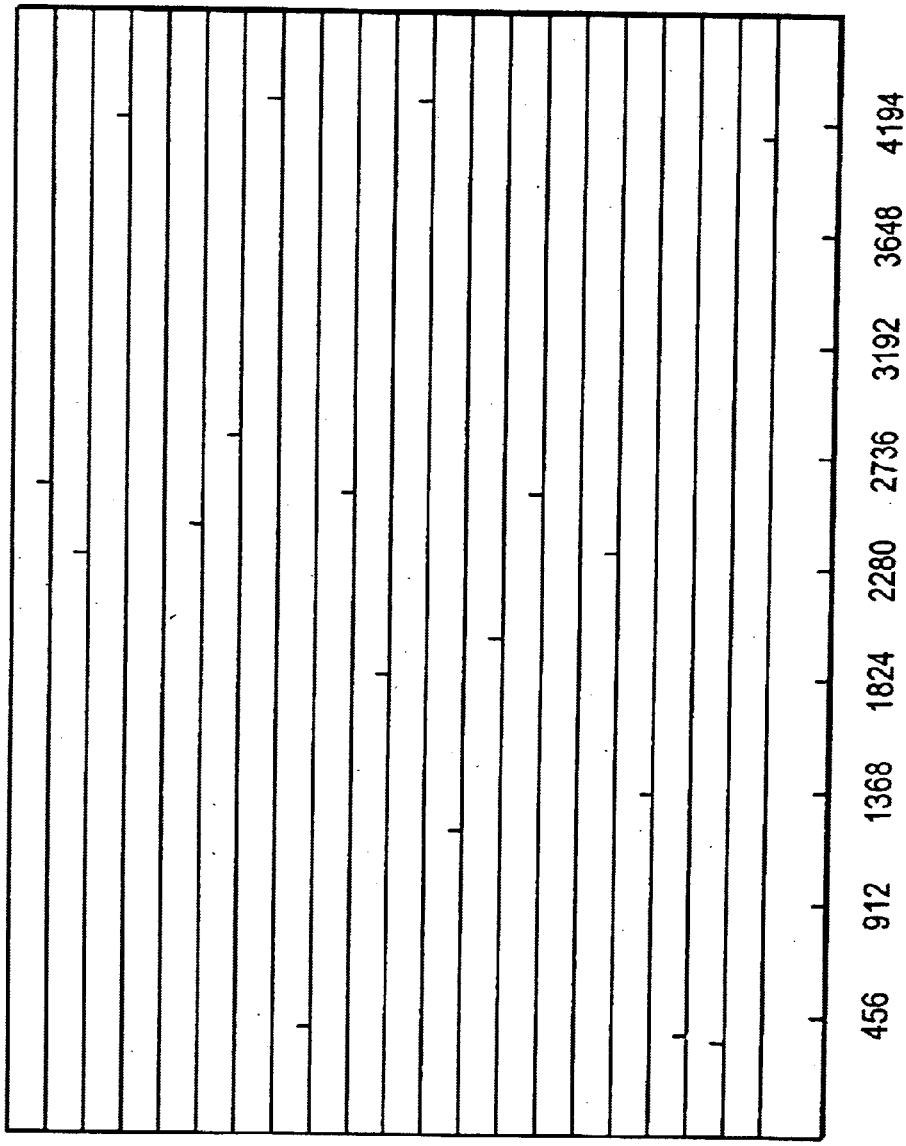

Staudenbauer, W.L. and Orr, E., "DNA gyrase: affinity chromatography on novobiocin–Sepharose and catalytic properties," Nucleic Acid Research, 9(15):3589–3603 (1981).

Studier, W.F. et al., "Use of T7 RNA Polymerase to Direct Expression of Cloned Genes," Methods In Enzymol. 185:60–89 (1990).

Wigley, D.B. et al., "Crystal structure of an N–terminal fragment of the DNA gyrase B protein," Nature 351:624–629 (1991).

Sigma Chemical Company, Product Catalog, p. 51 (1993).

* cited by examiner

TOPOISOMERASE IV, CORRESPONDING NUCLEOTIDE SEQUENCES AND USES THEREOF

This is a division of application Ser. No. 08/776,265, filed Jan. 24, 1997, now U.S. Pat. No. 6,001,631, which is incorporated herein by reference.

The present invention relates to a novel topoisomerase IV, the nucleotide sequences encoding this enzyme, their corresponding vectors and the use of this enzyme for screening biologically active products.

Topoisomerases are enzymes capable of modifying the topological configuration of DNA rings, of making knots therein or of interlacing separated rings. They are thus involved in the replication, transcription and recombination of the entire genetic information (Wang et al., 1990). The mechanism of all these topological conversions is the same: the ring is opened so that a segment of DNA passes through the gap before the ends are rejoined. Two types of topoisomerase are involved in these conversions: type I topoisomerases which cut a single DNA strand and type II topoisomerases which cut both strands simultaneously.

Up until now, two type II bacterial topoisomerases have been identified and studied more particularly: gyrase from *Escherichia coli* (Gellert et al., 1976), and more recently, DNA topoisomerase IV from *E. coli* (Kato et al., 1990).

Gyrase is a $\alpha_2\beta_2$ tetramer whose α or GyrA and β or GyrB subunits are encoded by the gyrA and gyrB genes respectively. Bacterial gyrases are the only known topoisomerases capable of supercoiling relaxed DNA rings in the presence of ATP.

As regards more particularly DNA topoisomerase IV from *E. coli*, it relaxes supercoiled plasmid DNA, unknots T4 phage DNA and unwinds (or decatenates) kinetoplast DNA (Kato et al., 1992; Peng et al., 1993). The sequence of its corresponding genes, parC and parE from *E. coli*, has made it possible to demonstrate regions of high similarity between the subunits of gyrase and those of this topoisomerase IV, ParC with GyrA (35.6% over the entire sequence) and ParE with GyrB (40.1% over the entire sequence) respectively (Kato et al., 1990).

*E. coli* gyrase has also been identified as being a primary target of fluoroquinolones (Hooper et al., 1993). It has thus been demonstrated that *E. coli* strains mutated at the level of the Ser83 residue in the GyrA subunit have a high resistance to fluoroquinolones (Maxwell, 1992). Fluoroquinolones bind less to DNA-mutated gyrase complexes than to DNA-wild-type gyrase complexes. Indeed, other point mutations, mapped in the region between residues 67 and 106 of GyrA, lead to strains resistant to fluoroquinolones. This region is called QRDR (Yoshida et al., 1990; Cullen et al., 1989). Similar results have been published with strains of *Staphylococcus aureus* resistant to fluoroquinolones (Goswitz et al., 1992; Sreedharan et al., 1990). Gyrase is therefore nowadays recognized as being the primary target of quinolones. However, a clinical strain of *Staphylococcus aureus*, not containing any mutation in the QRDR region of GyrA, has also been described as resistant to fluoroquinolones (Sreedharan et al., 1991).

Nowadays, this phenomenon of resistance developed by *Staphylococcus aureus* bacteria towards antibiotics and more particularly towards fluoroquinolones is being increasingly encountered at the therapeutic level. It would be particularly important to be able to lift this resistance and this involves a characterization of all the parameters which are associated with it.

The main objective of the present invention is precisely the identification, sequencing and characterization of nucleic sequences encoding subunits of a novel topoisomerase, topoisomerase IV of *Staphylococcus aureus*, composed of two subunits, GrlA and GrlB.

Unexpectedly, the applicant has found that the primary target of the fluoroquinolones in *S. aureus* is a topoisomerase IV and not gyrase. It has thus demonstrated that clinical strains of *S. aureus*, in which the QRDR region of the GyrA subunit of gyrase is identical to the wild-type sequence, develop nevertheless a resistance to fluoroquinolones because of a mutation which they possess in the region of the GrlA subunit of topoisomerase IV, homologous to the QRDR region.

The first subject of the present invention is a nucleotide sequence encoding at least one subunit of topoisomerase IV of *Staphylococcus aureus*.

The present invention describes in particular the isolation and the characterization of the grlA and grlB genes. These genes have been cloned, sequenced and expressed in *E. coli*, and their enzymatic activity has been characterized. They were isolated from a *Staphylococcus aureus* genomic DNA library. From the grlAB nucleic sequence (SEQ ID No. 1 and SEQ ID No. 2), two open frames, corresponding to the grlB and grlA genes respectively, have been identified. The grlA and grlB genes have been sequenced in SEQ ID No. 4 and SEQ ID No. 6 respectively.

Preferably, the subject of the present invention is a nucleotide sequence chosen from:

(a) all or part of the grlA (SEQ ID No. 4) or grlB (SEQ ID No. 6) genes, (b) the sequences hybridizing with all or part of the (a) genes and encoding a subunit of a topoisomerase IV, and (c) the sequences derived from the (a) and (b) sequences because of the degeneracy of the genetic code.

It is clear that from the genes identified in the present application, it is possible, by hybridization, to directly clone other genes encoding a subunit of topoisomerase IV of bacteria close to *S. aureus* such as for example Streptococci and Enterococci. It is thus possible to clone this type of gene using, as probe, the genes grlA, grlB or fragments thereof. Likewise, the cloning of these genes may be carried out using degenerate oligonucleotides derived from sequences of the grlA or grlB genes or fragments thereof.

For the purposes of the present invention, derivative is understood to mean any sequence obtained by one or more modifications and encoding a product conserving at least one of the biological properties of the original protein. Modification should be understood to mean any mutation, substitution, deletion, addition or modification of a genetic and/or chemical nature. These modifications may be performed by techniques known to persons skilled in the art.

Among the preferred derivatives, there may be mentioned more particularly natural variants, molecules in which one or more residues have been substituted, derivatives obtained by deletion(s) of regions not or little involved in the interaction between the binding sites considered or expressing an undesirable activity, and derivatives having, compared with the native sequence, one or more additional residues.

Still more preferably, the subject of the invention is the nucleotide sequences represented by the grlA (SEQ ID No. 4) and grlB (SEQ ID No. 6) genes.

It also relates to any grlA gene having a mutation leading to a resistance to molecules of the quinolone and more particularly of the fluoroquinolone family. As a representative of these mutated genes, there may be mentioned more particularly the grlA gene having a base change from C to A at position 2270 of SEQ ID No. 4. The resulting gene is termed grlA$_{(C-2270A)}$. This mutation leads to substitution of the Ser-80 residue with Tyr in the GrlA protein. The resulting protein will be designated by GrlA$_{(Ser-80\ Tyr)}$.

Another subject of the present invention relates to a recombinant DNA comprising at least one nucleotide sequence encoding a subunit of topoisomerase IV of *Staphylococcus aureus*. More particularly, it is a recombinant DNA comprising at least one nucleotide sequence as defined above in (a), (b) and (c) and more particularly the gene grlA (SEQ ID No. 4) grlA$_{(C-2270A)}$ and/or the gene grlB (SEQ ID No. 6).

According to a preferred mode of the invention, the nucleotide sequences defined above form part of an expression vector which may be autonomously replicating or integrative.

Another subject of the invention relates to the polypeptides resulting from the expression of the nucleotide sequences as defined above. More particularly, the present invention relates to the polypeptides comprising all or part of the polypeptides GrlA (SEQ ID No. 2) or GrlB (SEQ ID No. 3) or of their derivatives. For the purposes of the present invention, the term derivative designates any molecule obtained by modification of the genetic and/or chemical nature of the peptide sequence. Modification of the genetic and/or chemical nature may be understood to mean any mutation, substitution, deletion, addition and/or modification of one or more residues. Such derivatives may be generated for different purposes, such as especially that of increasing the affinity of the peptide for its substrate(s), that of enhancing its production levels, that of increasing its resistance to proteases, that of increasing and/or of modifying its activity, or that of conferring new biological properties on it. Among the derivatives resulting from an addition, there may be mentioned, for example, the chimeric polypeptides containing an additional heterologous part attached to one end. The term derivative also comprises the polypeptides homologous to the polypeptides described in the present invention, derived from other cellular sources.

Preferably, they are the polypeptides GrlA (SEQ ID No. 3), GrlB (SEQ ID No. 5) and GrlA$_{(Ser-80Tyr)}$.

The subject of the invention is also any recombinant cell containing a nucleotide sequence, a recombinant DNA and/or a vector as defined above. The recombinant cells according to the invention may be both eukaryotic and prokaryotic cells. Among the suitable eukaryotic cells, there may be mentioned animal cells, yeasts, or fungi. In particular, as regards yeasts, there may be mentioned yeasts of the genus Saccharomyces, Kluyveromyces, Pichia, Schwanniomyces or Hansenula. As regards animal cells, there may be mentioned COS, CHO and C127 cells, Xenopus eggs, and the like. Among the fungi, there may be mentioned more particularly Micromonospora, Aspergillus ssp. or Trichoderma ssp. Preferably, they are prokaryotic cells. In this case, the following bacteria may be more particularly used: Actinomycetes, Bacillus, and more preferably *E. coli* and Staphylococcus. The recombinant cells of the invention may be obtained by any method allowing the introduction of a foreign nucleotide sequence into a cell. This may be especially transformation, electroporation, conjugation, fusion of protoplasts, or any other technique known to persons skilled in the art.

The subject of the present invention is also a process for the preparation of polypeptides as claimed from the culture of one of these recombinant cells. The polypeptide(s) thus obtained are recovered according to conventional methods after the culture.

The invention also relates to an isolated topoisomerase IV capable of being obtained from the expression of all or part of the grlA gene (SEQ ID No. 4) and of all or part of the grlB gene (SEQ ID No. 6) or of their respective derivatives.

Derivative is understood to designate the sequences hybridizing with all or part of the grlA or grlB gene and encoding a subunit of a topoisomerase IV as well as all the sequences derived from a degeneracy of the genetic code of these hybrid sequences or of the sequences corresponding to all or part of the grlA or grlB gene.

More preferably, it is an isolated topoisomerase IV derived from the expression of all or part of the grlA gene (SEQ ID No. 4) or of all or part of the grlB gene (SEQ ID No. 6).

The present invention relates more particularly to any topoisomerase IV behaving as a primary target towards fluoroquinolones.

According to a specific mode of the invention, it is topoisomerase IV of *Staphylococcus aureus*.

The claimed topoisomerase IV according to the invention is most particularly useful for targeting biologically active products such as for example potential antibiotics and especially molecules of the fluoroquinolone family. Advantageously, it may also be used to assay and/or identify products inhibiting the ATP-dependent DNA relaxing reaction and/or the products inhibiting the reaction of decatenation of catenanes of DNA.

The applicant has thus developed an assay for enzymatic activity which is specific for topoisomerase IV of *S. aureus* and has shown that this activity is inhibited by antibiotic molecules such as fluoroquinolones.

The present invention provides a new target for searching for new antibiotics, as well as a screen specific for this target; this screen is described in Example 7. This screen makes it possible to demonstrate the products which inhibit DNA topoisomerase IV of *S. aureus*. The following may be used in this test: pure or mixed synthetic products, natural plant extracts, bacterial cultures, fungi, yeasts or algae, pure or in the form of a mixture. The test described in the present invention makes it possible to detect both products which stabilize the cleavable complex, a reaction intermediate of the reaction catalysed by the enzyme, and also inhibitors acting through other mechanisms.

The examples and figures presented below by way of nonlimiting illustration show other advantages and characteristics of the present invention.

LEGEND TO THE FIGURES

FIG. 1: Restriction map of the 4565 bp fragment containing the grlB and grlA genes of *S. aureus*.

Figure 2:
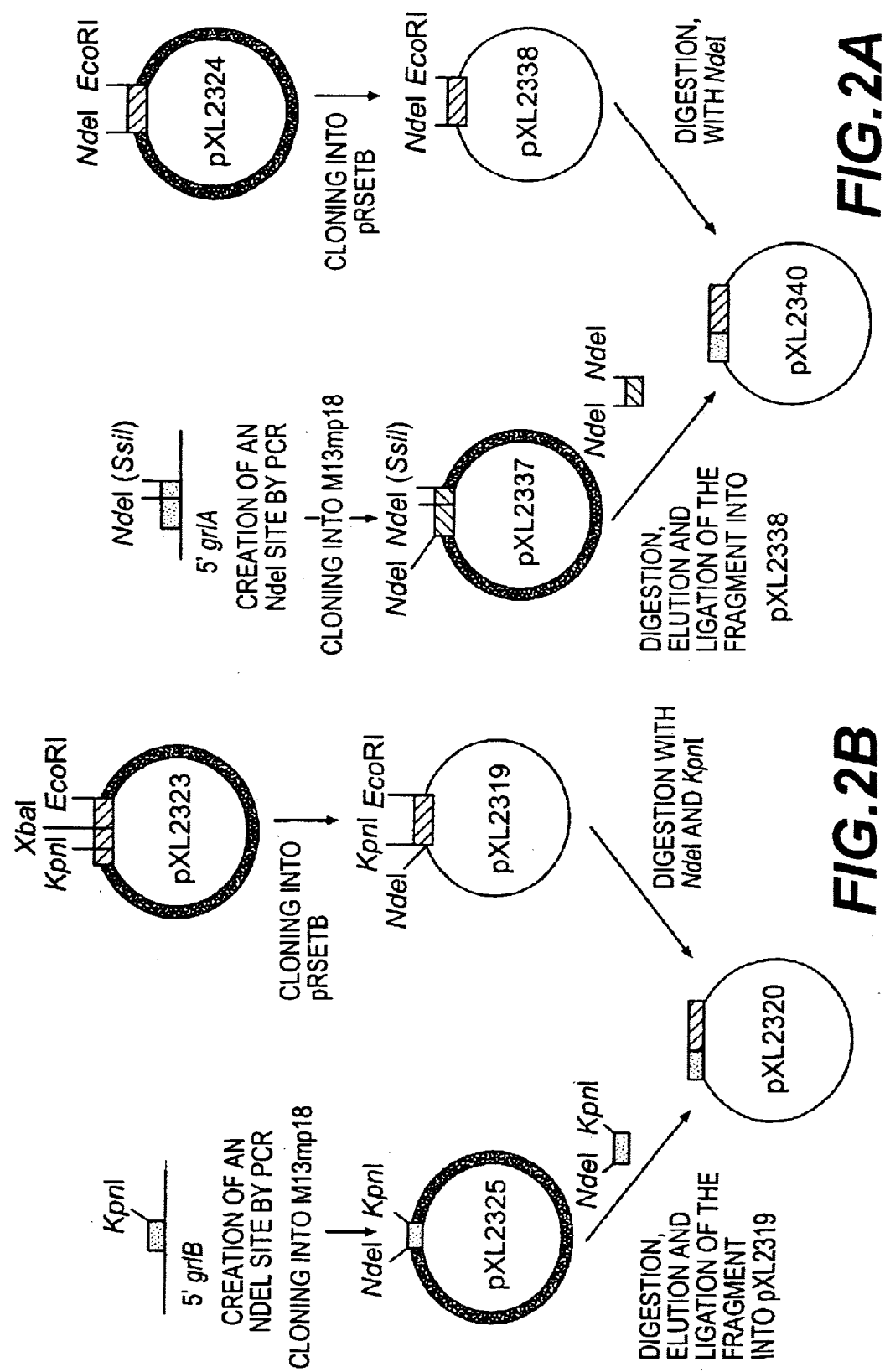

FIGS. 2A and B: Construction of the plasmids for expression of grlA and grlB. The constructs produced with grlA are schematically represented in A and those of grlB are in B. The cloned *S. aureus* DNA is represented by the shaded rectangles, the vectors derived from M13 are in a thick black line and the expression vectors are in a fine black line, the SstI restriction site is in brackets because it is a cloning site.

Figure 3:
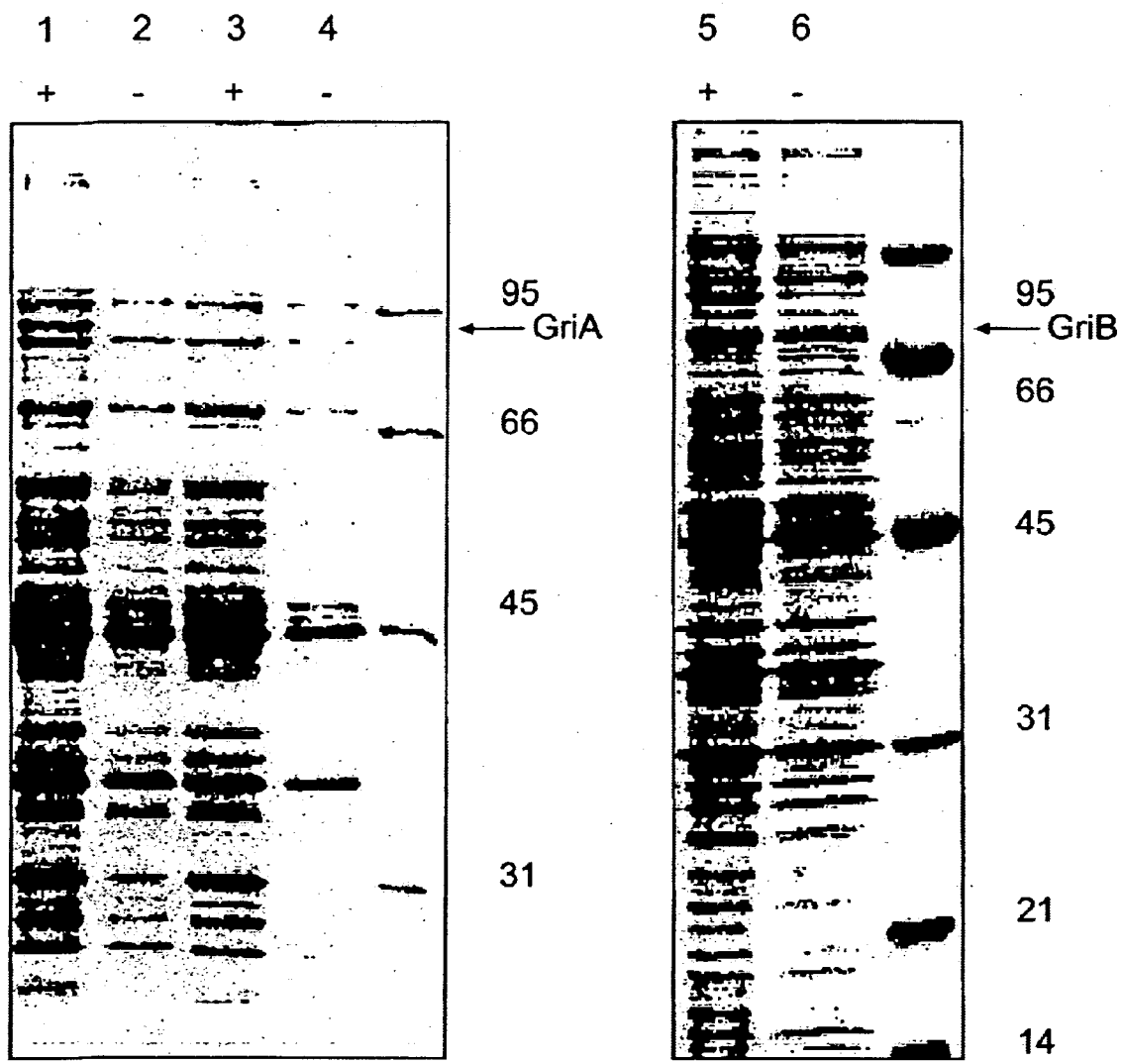

FIG. 3: PAGE-SDS electrophoresis gel stained with Coomasie blue. Total cell extracts are deposited, lanes: 1 and 2, XL1-blue, pXL2340; 3 and 4, XL1-blue, pRSETB; 5 and 6, XL1-blue, pXL2320. The molecular weight markers (in hundreds) are indicated on the right of the figure. The arrow shows the overproduced protein. The + or − signs represent the induction with or without IPTG.

Figure 4:
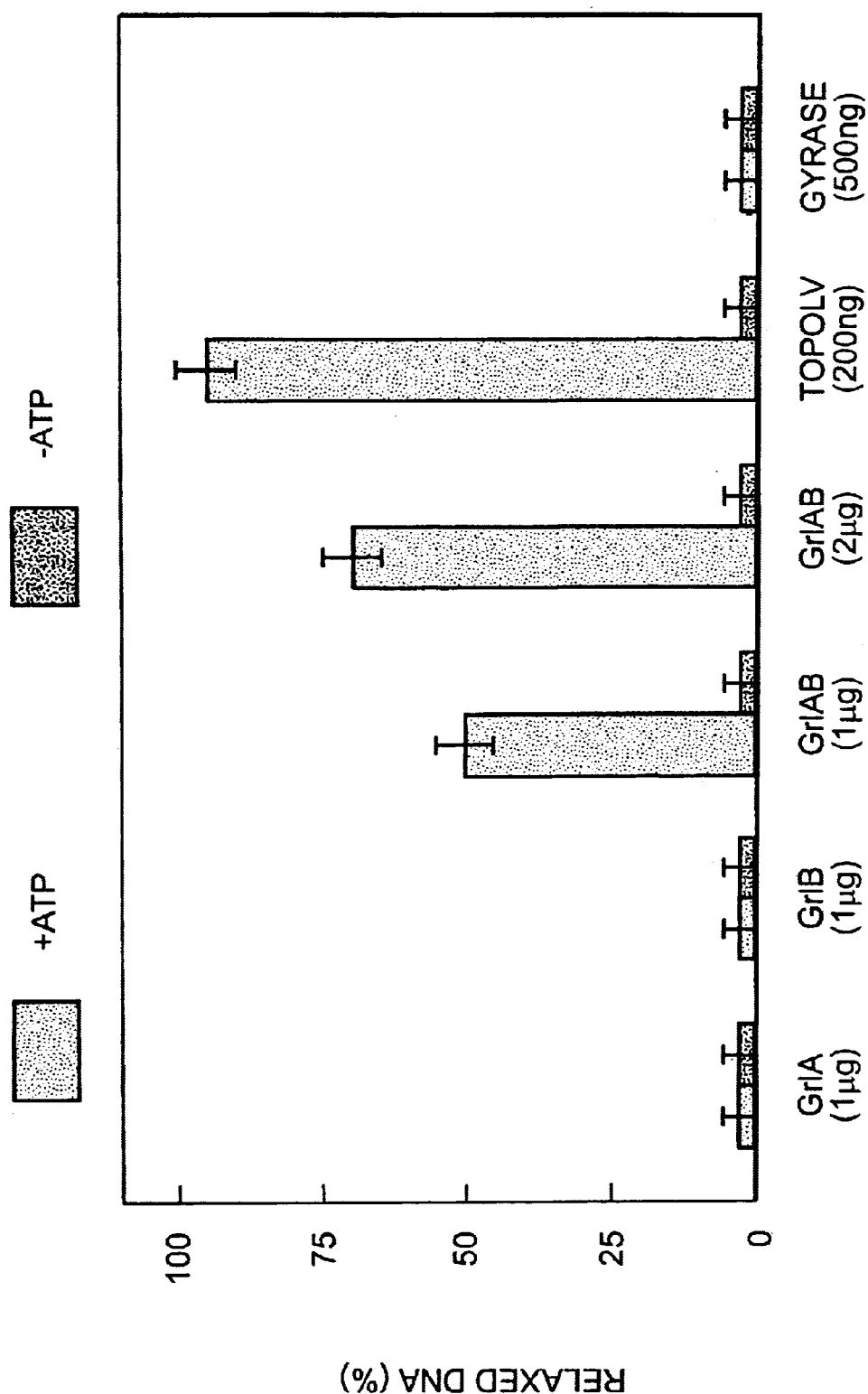

FIG. 4: ATP-dependent relaxation activity of the GrlAB protein. The control experiments with purified DNA topoisomerase IV of *E. coli* (Peng and Marians, 1993) and purified DNA gyrase of *E. coli* (Hallet et al., 1990) are also described.

Figure 5:
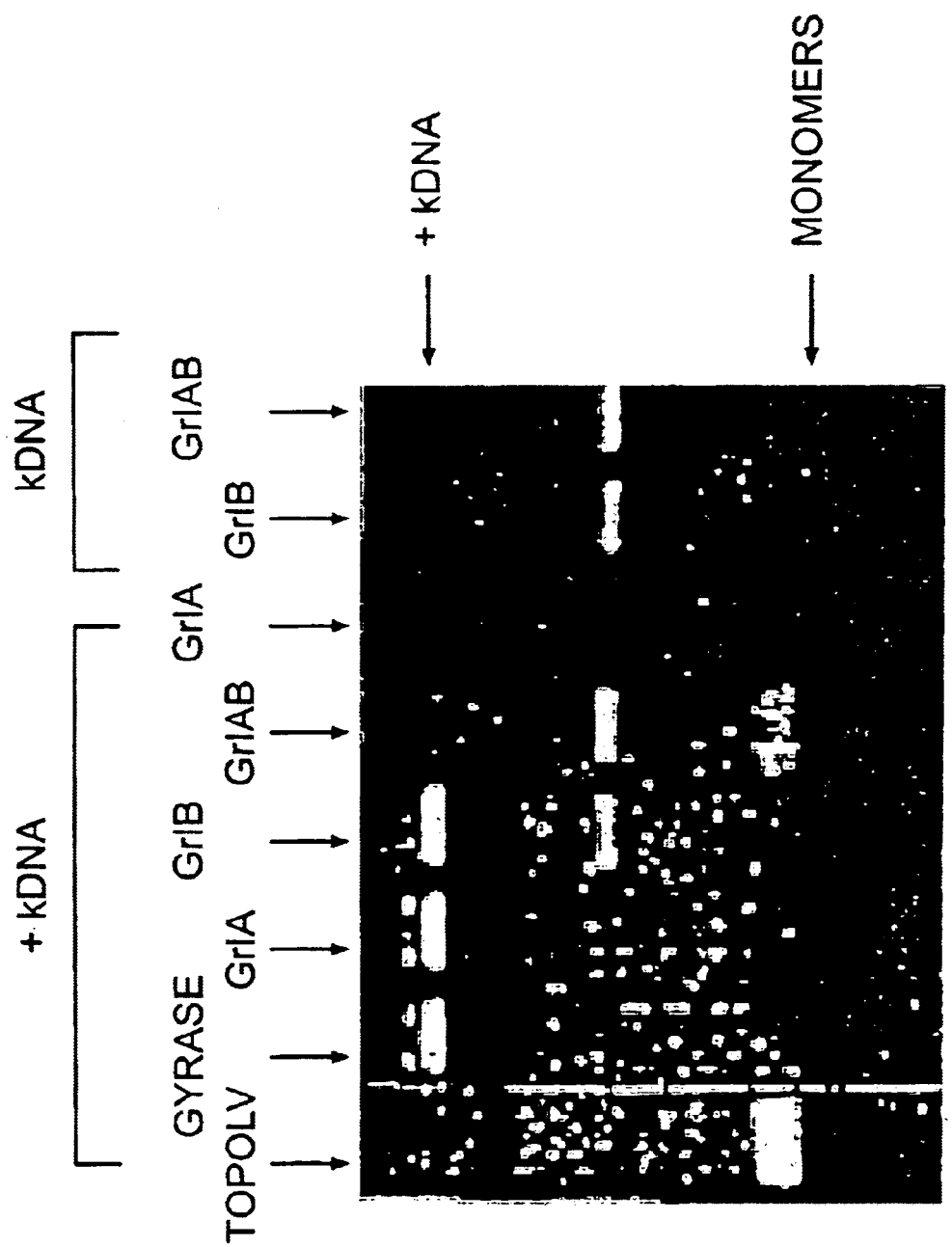

FIG. 5: Decatenation activity of the protein GrlAB. kDNA, kinetoplast DNA; monomers, relaxed and decatenated DNA monomers. TopoIV: purified DNA topoisomerase IV of E. coli (50 ng); Gyrase: purified DNA gyrase of E. coli (50 ng); GrlA: GrlA protein extract (2 μg); GrlB: GrlB protein extract (2 μg); GrlAB: GrlA protein extract (2 μg) mixed with the GrlB protein extract (2 μg).

EXAMPLE 1

PCR amplification of DNA fragments of
Staphylococcus aureus which are inside the grlA
and grlB genes This example describes the production of DNA fragments of Staphylococcus aureus which are inside the grlA and grlB genes. These fragments were obtained after PCR amplification carried out at 50° C. with genomic DNA of the Staphylococcus aureus strain RN4220 (Novick, 1990) and of the degenerate oligonucleotides corresponding to the amino acids conserved in the N-terminal regions of the subunits GyrA of E. coli and B. subtilis and ParC of E. coli or of the subunits GyrB of E. coli and B. subtilis and ParE of E. coli. More specifically, the sense oligonucleotides 2137 and antisense oligonucleotides 2135 made it possible to amplify fragments of 255 bp which can encode 85 amino acids which would correspond to positions 39 to 124 on the E. coli GyrA sequence; the sequence of the sense oligonucleotide 2137 is 5'-GCGCGAATTC GATGG(A,T)(C,T)T-(A,T)AAACC(A,T)GT(A,T)CA-3' (SEQ ID No. 7) and that of the antisense 2135 is 5'-CGCG AAGCTTTTC(T,A)GTATA(A,T)C-(T,G)CAT(A,T)GC (A,T)GC-3' (SEQ ID No. 8). The oligonucleotides 2144 and 2138 led to the amplification of 1 kb fragments which can encode 333 amino acids which would correspond to positions 98 to 430 on the E. coli GyrB sequence; the sequence of the sense oligonucleotide 2144 is 5'-GCGC GAATTCT(T,A)CATGC(A,T)GG(T,A)GG(T,A)AAATT-3' (SEQ ID No. 9), and that of the antisense 2138 is 5'-CGCG AAGCTT(T,A)CC(T,A)CC(T,A)GC(T,A)GAATC(T,A)CC TTC-3' (SEQ ID No. 10). The fragments were cloned and a total of 40 clones were analysed by sequencing their insert. The sequence of the oligonucleotides used for the PCR was found for 31 clones out of 40; among the 31 clones, 20 have a sequence which is inside the gyrA or gyrB gene of S. aureus; the other 11 clones contain either a fragment A of 255 bp or a fragment B of 1 kb.

The amino acid sequence which the A fragment is thought to encode has 59% identity with the GyrA subunit of S. aureus between positions 44 to 125, the A fragment is therefore thought to be part of an S. aureus grlA gene thus newly identified. Likewise, the amino acid sequence which the B fragment is thought to encode has 51% identity with the GyrB subunit of S. aureus between positions 105 to 277, the B fragment is therefore thought to be part of an S. aureus grlB gene thus newly identified.

EXAMPLE 2

Cloning and sequencing of the grlA and grlB genes
of Staphylococcus aureus

This example describes the molecular biology experiments which have made it possible to clone and then sequence the grlA and grlB genes of Staphylococcus aureus.

The A and B fragments described in Example 1 were used as radioactive probe to identify, by hybridization, the grlA and grlB genes in a genomic DNA library of S. aureus FDA 574 (CE ent⁺) constructed in λgt11 by Clontech Laboratories (catalogue XL1501b, batch 0721). Out of a total of 250,000 recombinant phages, twelve phages hybridize with the A fragment or the B fragment but do not hybridize with oligonucleotides specific for the gyrA or gyrB genes. The size of the EcoRI inserts contained in these phages varies between 0.7 and 3.5 kb and two phages, 16 and 111, whose insert is of a larger size, were studied. The EcoR1 insert of 3.5 kb of the phage 16 was eluted and then digested with XbaI and the two fragments of 1.5 and 2 kb were cloned into M13mp19 and M13mp18 (Boehringer Mannheim) in order to generate pXL2321 and pXL2322. Likewise, the EcoRI insert of 3.6 kb of the phase 111 was eluted and then digested with PstI and the 2 kb fragment was cloned into M13mp19 in order to generate pXL2324.

The inserts contained in the recombinant phages pXL2321, pXL2322 and pXL2324 were sequenced on both strands with the aid of the universal primer or of internal oligonucleotides using the Sanger method. The nucleic sequence grlAB (SEQ ID No. 1 and SEQ ID No. 2) of 4565 bp was analysed with the programme by Staden et al., 1982 in order to identify the coding sequences with the aid of a codon usage table for S. aureus. Only two open frames ORF1 (positions 41 to 2029) and ORF2 (positions 2032 to 4431) were thus determined. In SEQ ID NO:1, which is the coding strand, the open frame ORF1 starts arbitrarily at ATG position 41 but it can also start at TTG position 17 or 35, this codon being already described as initiation codon in S. aureus; the stop codon of ORF1 overlaps with the initiation codon GTG of ORF2, which is characteristic of a translational coupling (Normark et al., 1983); such a coupling has, for example, been described for the gyrA and gyrB genes of Haloferax sp. (Holmes et al., 1991). These open frames have a percentage of GC of 34.5% which is a value in agreement with the values described for the S. aureus DNA in the literature (Novick, 1990). Moreover, the B fragment is identical to the sequence described on SEQ ID No. 1 from position 333 to position 1348 in ORF1 and the fragment A is identical to the sequence of SEQ ID No. 1 from position 2137 to position 2394 in ORF2. From the nucleotide sequence, a restriction map is produced with enzymes which cut least frequently, see FIG. 1.

This sequence analysis shows that ORF1 is the grlB gene and ORF2 the grlA gene.

EXAMPLE 3

Primary structure, expression and function of the
GrlA and GrlB proteins encoded by the grlA and
grlB genes of Staphylococcus aureus This example describes the primary structure, the expression of E. coli and the function of the GrlA and GrlB proteins of Staphylococcus aureus. This function, which corresponds to a DNA topoisomerase IV, is based, in this example, on sequence homology and genetic complementation data.

3.1—Primary Structure and Sequence Analysis of
the GrlA and GrlB Proteins

This example describes computer analysis of the sequence of the grlA and grlB genes of Staphylococcus aureus carried out using the sequence data presented in Example 2. The grlB gene encodes a GrlB protein of 663 amino acids (molecular weight 74,318), and the grlA gene encodes a GrlA protein of 800 amino acids (molecular weight 91,040). The coding parts of the grlB and grlA genes, the sequences of the GrlB and GrlA proteins are presented in SEQ ID No. 5 and SEQ ID No. 3 respectively and the properties of each of these proteins (amino acid composition, isoelectric point, polarity index) are presented in Tables 1 and 2 below.

Protein: GrlA:

| | |
|---|---|
| First residue = 1 and last residue | = 800 |
| Molecular mass (monoisotopic) | = 91040.8438 |
| Molecular mass (average) | = 91097.2578 |
| Polarity index (%) | = 52.00 |
| Isoelectric point | = 6.77 |
| OD 260 (1 mg/ml) = 0.298 | OD 280 (1 mg/ml) = 0.487 |

TABLE 1

| | | | NUMBER | % NOMB | WEIGHT | % WEIGHT |
|---|---|---|---|---|---|---|
| 1 | Phe | F | 22 | 2.75 | 3235.51 | 3.55 |
| 2 | Leu | L | 74 | 9.25 | 8368.22 | 9.19 |
| 3 | Ile | I | 77 | 9.63 | 8707.47 | 9.56 |
| 4 | Met | M | 19 | 2.38 | 2489.77 | 2.73 |
| 5 | Val | V | 59 | 7.38 | 5945.04 | 6.42 |
| 6 | Ser | S | 51 | 6.38 | 4439.63 | 4.88 |
| 7 | Pro | P | 22 | 2.75 | 2135.16 | 2.35 |
| 8 | Thr | T | 43 | 5.38 | 4345.05 | 4.77 |
| 9 | Ala | A | 37 | 4.63 | 229.37 | 2.89 |
| 10 | Tyr | Y | 28 | 3.50 | 4565.77 | 5.02 |
| 12 | His | H | 20 | 2.50 | 2741.18 | 3.01 |
| 13 | Gln | Q | 26 | 3.25 | 3329.52 | 3.66 |
| 14 | sn | N | 45 | 5.63 | 5131.93 | 5.64 |
| 15 | Lys | K | 66 | 8.25 | 9454.27 | 9.29 |
| 16 | Asp | D | 54 | 6.75 | 6211.45 | 6.82 |
| 17 | Glu | E | 67 | 8.38 | 8645.85 | 9.50 |
| 18 | Cys | C | 0 | 0.00 | 0.00 | 0.00 |
| 19 | Trp | W | 2 | 0.25 | 372.16 | 0.41 |
| 20 | Arg | R | 44 | 5.50 | 6868.45 | 7.54 |
| 21 | Gly | G | 44 | 5.50 | 2509.94 | 2.76 |

GrlB protein:

| | |
|---|---|
| First residue = 1 and last residue | = 663 |
| Molecular mass (monoisotropic) | = 74318.3516 |
| Molecular mass (average) | = 74363.9219 |
| Polarity index (%) | = 53.70 |
| Isoelectric point | = 7.21 |
| OD 260 (1 mg/ml) = 0.404 | OD 280 (1 mg/ml) = 0.603 |

TABLE 2

| | | | NUMBER | % NOMB | WEIGHT | % WEIGHT |
|---|---|---|---|---|---|---|
| 1 | Phe | F | 26 | 3.92 | 3823.78 | 5.15 |
| 2 | Leu | L | 55 | 8.30 | 6219.62 | 8.37 |
| 3 | Ile | I | 36 | 5.43 | 4071.03 | 5.48 |
| 4 | Met | M | 10 | 1.51 | 1310.40 | 1.76 |
| 5 | Val | V | 50 | 7.54 | 4953.42 | 6.67 |
| 6 | Ser | S | 41 | 6.18 | 3568.31 | 4.80 |
| 7 | Pro | P | 15 | 2.26 | 1455.79 | 1.96 |
| 8 | Thr | T | 41 | 6.18 | 4142.95 | 5.57 |
| 9 | Ala | A | 33 | 4.98 | 2344.22 | 3.15 |
| 10 | Tyr | Y | 19 | 2.87 | 3098.20 | 4.17 |
| 12 | His | H | 14 | 2.11 | 1918.82 | 2.58 |
| 13 | Gln | Q | 26 | 3.92 | 3329.52 | 4.48 |
| 14 | Asn | N | 36 | 5.43 | 4105.55 | 5.52 |
| 15 | Lys | K | 63 | 9.50 | 8069.98 | 10.86 |
| 16 | Asp | D | 40 | 6.03 | 4601.08 | 6.19 |
| 17 | Glu | E | 61 | 9.20 | 7871.60 | 10.59 |
| 18 | Cys | C | 0 | 0.00 | 0.00 | 0.00 |
| 19 | Trp | W | 4 | 0.60 | 744.32 | 1.00 |
| 20 | Arg | R | 34 | 5.13 | 5307.44 | 7.14 |
| 21 | Gly | G | 59 | 8.90 | 3364.27 | 4.53 |

The Kanehisa programme, described in 1984, was used to align the GrlB and GrlA proteins with the following type II bacterial DNA topoisomerases, the E. coli, B. subtilis or S. aureus gyrases or the E. coli topoisomerase IV. The degrees of identity, see Table 3, are high and are between 32 and 55%. More specifically, GrlB exhibits a greater degree of identity with the GyrB subunits of E. coli (49%) and of S. aureus (52%) than with ParE of E. coli (38%), whereas GrlA exhibits comparable degrees of identity with the GyrA subunits of E. coli (32%) and of S. aureus (39%) than with ParE of E. coli (33%).

The GyrB subunits of Staphylococcus aureus (Margerrison et al., 1992), Bacillus subtilis (Moriya et al., 1985), and Escherichia coli (Adachi et al., 1987) are called SAGYRB, BSGYRB and ECGYRB respectively, GrlB is called SAGRLB and ECPARE corresponds to ParE of E. coli (Kato et al., 1990). A similar nomenclature is used for the GyrA, GrlA and ParC subunits. The numbers under the name of the proteins are the numbers of amino acids in them.

TABLE 3

| B or B-like subunits | SAGYRB | SAGRLB | BSGYRB | ECGYRB |
|---|---|---|---|---|
| | 644 | 663 | 638 | 804 |
| SAGRLB | 52% | | | |
| BSGYRB | 68% | 55% | | |
| ECGYRS | 55% | 49% | 57% | |
| ECPARE | 40% | 38% | 40% | 40% |
| A or A-like subunits | SAGYRA | SAGRLA | BSGYRA | ECGYRA |
| | 887 | 800 | 821 | 875 |
| SAGRLA | 39% | | | |
| BSGYRA | 65% | 40% | | |
| ECGYRA | 39% | 32% | 41% | |
| ECPARC | 38% | 33% | 36% | 32% |

Multiple alignments between the type II bacterial topoisomerases, performed with the CLUSTAL programme of Higgins et al., 1988, show numerous conserved regions between the sequences of the various B, GrlB and ParE subunits and in the N-terminal part of the sequence of the A, GrlA and ParC subunits. The residues conserved in the N-terminal region of the B subunits of these proteins are in fact the residues involved in the binding of ATP and identified from X-ray crystallization data with the E. coli GyrB (Wigley et al., 1991). The residues conserved in the N-terminal region of the A subunits of these proteins are either the residues AAMRYTE (SEQ ID No. 11) close to the active site of gyrase Tyr-122, identified on the E. coli GyrA (Horowitz et al., 1987), or the residues YHPHGDS (SEQ ID No. 12) modified in the strains resistant to fluoroquinolones (Hooper et al., 1993).

3.2—Expression of the grlA and grlB Genes in E. coli

This example describes the constructs produced in order to express, in E. coli, the grlA or grlB genes under the control of the pT7 promoter (Studier et al., 1990). The expression plasmid pXL2320, see FIG. 2, containing the grlB gene in the vector pRSETB (Studier et al., 1990; Invitrogen) was constructed by cloning 1) the 1 kb EcoRI- XbaI insert of pXL2321 into pXL2322 at the XbaI and EcoRI sites in order to generate pXL2323; 2) the 1.9 kb KpnI-EcoRI insert of pXL2323 at the KpnI and EcoRI sites of the vector pRSETB in order to generate pXL2319; the 0.5 kb NdeI-KpnI insert of pXL2325 at the NdeI and KpnI sites of pXL2319 in order to obtain pXL2320. (pXL2325 contains the first 500 bases of the gene where a CAT sequence has been introduced by mutagenesis, just upstream of the ATG initiation codon, in order to create a NdeI site). The grlB gene expression cassette contained in pXL2320 was cloned at the BglII and EcoRI sites of pKT230 (Bagdasarian et al., 1981) in order to obtain pXL2439. The expression plasmid pXL2340, see FIG. 2, containing the grlA gene in the vector pRSETB was constructed by cloning 1) the 1.7 kb NdeI-EcoRI insert of pXL2324 at the NdeI and EcoRI sites of the vector pRSETB in order to generate pXL2338; the 0.75 kb NdeI insert of pXL2337 at the NdeI sites of pXL2338 in order to obtain pXL2340. (pXL2337 contains the first 750 bases of the gene where a CATATG sequence has been introduced by mutagenesis, in place of the GTG initiation codon in order to create an NdeI site).

The plasmids pXL2320, or pXL2340 were introduced into the *E. coli* XL-1-Blue strain (Stratagen) and the expression of the genes was induced when the T7 phage RNA polymerase was produced after induction of the gene, encoding the T7 phage RNA polymerase, cloned into the helper phage M13/T7 (Studier et al., 1990, Invitrogen). The cellular extracts were analysed by electrophoresis on a PAGE-SDS gel stained with Coomasie blue as has already been described (Denèfle et al., 1987). In FIG. 3 is represented the production of a protein with a i) molecular weight of 79,000, when the grlB gene is induced in the *E. coli* strain XL1-blue, pXL2320; and ii) molecular weight of 90,000, when the grlA gene is induced in the *E. coli* strain XL1-Blue, pXL2340. The measured molecular weights are in agreement with the molecular weights deduced from the sequence.

3.3—Complementation of the parCts and parEts Mutants of *Salmonella typhimurium* by the grlA and grlB Genes of *Staphylococcus aureus*

This example describes the heterologous complementation of the *S. typhimurium* parCts and parEts mutants by the *S. aureus* grlA and grlB genes. The plasmids pXL2320, pXL2340, pXL2439 or the vector pRSETB were introduced into the *S. typhimurium* strains SE7784 (parC281(Ts) zge-2393::Tn10 leu485) or Se8041 (parE206(Ts) zge-2393::Tn10 leu485) (Luttinger et al., 1991). No plasmid complements the heat-sensitive phenotype; on the other hand, when the plasmids pXL2340 and pXL2439 are introduced simultaneously into the SE7784 strain or into the SE8041 strain, the heat-sensitive phenotype of both strains is complemented. Consequently, the coexpression of the grlA and grlB genes of *S. aureus* allows the complementation of the ParC Ts or ParE Ts phenotype of the *S. typhimurium* mutants.

EXAMPLE 4

The DNA topoisomerase IV of *S. aureus* is the primary target of the fluoroquinolones This example describes the presence of a point mutation Ser-80 in the GrlA subunit with all the analysed clinical strains of *S. aureus* resistant to the fluoroquinolones whereas a mutation in the QRDR region (Quinolone Determining Region) (equivalent to the Ser-80 region of GrlA) in the GyrA subunit does not exist with the clinical strains of *S. aureus* weakly resistant to the fluoroquinolones. Consequently, the GrlA subunit is shown to be the primary target of the fluoroquinolones in *S. aureus*.

The genomic DNA of eight clinical strains of *S. aureus* and of a laboratory strain was prepared and used to amplify at 42° C. by PCR: i) the first 500 base pairs of gyrA using the sense oligonucleotide 5'-GGC<u>GGATCCC</u>ATATGGCT GAATTACCTCA-3' (SEQ ID No. 13) and the antisense oligonucleotide 5'-GGC<u>GGAAT TC</u>GACGGCTCTCTTT CATTAC-3' (SEQ ID No. 14); ii) and the first 800 base pairs of grlA using the sense oligonucleotide 5'-GGCC <u>GGATCCCATATG</u>AGTGAAATAATT CAAGATT-3' (SEQ ID No. 15) and the antisense oligonucleotide -5'-GGCC <u>GAATTCTAATAATTAACTGTTTACGTCC</u>-3' (SEQ ID No. 16). Each amplified fragment was cloned into the phage M13mp18 and the sequence of the first 300 base pairs of each of the genes was read on 2 clones. The gyrA sequence is identical to that published by Magerrison and that of grlA to that described in SEQ ID No. 1, with the exception of the mutations presented in Table 4. The mutations in gyrA exist with the strains highly resistant to fluoroquinolones (SA4, SA5, SA6, SA35, SA42R and SA47; MIC for ciprofloxacin>16 mg/l); these mutations are a base change which leads to changes in the amino acids Ser-84 or Ser-85 or Glu-88. A mutation in grlA exists with all the strains resistant to fluoroquinolones and corresponds to the changing of the residue Ser-80 to Phe or Tyr.

TABLE 4

| Strain | MIC mg/l Cipro-floxacin | Mutation in gyrA | | Mutation in grlA | |
| --- | --- | --- | --- | --- | --- |
| | | Base | Codon | Base | Codon |
| RN4220* | 1 | no | no | no | no |
| SA42* | 0.5 | no | no | no | no |
| SAH** | 2 | no | no | 2281 G→A | $^{84}$Glu→Lys |
| SA1* | 2 | no | no | 2270 C→T | $^{80}$Ser→Phe |
| SAA** | 4 | no | no | 2281 G→A | $^{84}$Glu→Lys |
| SA3** | 4 | no | no | 2270 C→T | $^{80}$Ser→Phe |
| SA2** | 16 | no | no | 2270 C→A | $^{80}$Ser→Tyr |
| SA47* | 16 | 2533 C→T* | $^{84}$Ser→Leu | 2270 C→A | $^{80}$Ser→Tyr |
| SA4** | 32 | 2544 C→T* | $^{88}$Glu→Lys | 2270 C→T | $^{80}$Ser→Phe |
| SA5** | 32 | 2533 C→T* | $^{84}$Ser→Leu | 2270 C→T | $^{80}$Ser→Phe |
| SA6** | 32 | 2533 C→T* | $^{84}$Ser→Leu | 2270 C→T | $^{80}$Ser→Phe |
| SA35* | 64 | 2535 C→T* | $^{85}$Ser→Pro | 2270 C→A | $^{80}$Ser→Tyr |
| SA42R* | >128 | 2533 C→T* | $^{84}$Ser→Leu | 2270 C→A | $^{80}$Ser→Tyr |

*already published by Sreedharan et al. (1990)
**strains obtained from French state hospitals.

EXAMPLE 5

PCR (Polymerase Chain Reaction) amplification of the *S. aureus* DNA fragment which is inside grlA containing a point mutation which leads to a substitution in GrlA from Ser-80 to Tyr (Ser-80→Tyr)

This example describes the production of the DNA fragment which is inside grlA of an *S. aureus* strain, SA2, resistant to fluoroquinolones. The grlA fragment contains a base change from C to A at position 2270 of the wild-type gene (FIG. 1). This mutation leads to a substitution of the residue Ser-80 to Tyr in the GrlA protein. It has been shown that a substitution of the residue Ser-80 to Phe or Tyr exists with all the strains weakly resistant to fluoroquinolones (Example 4). The fragment which is inside grlA was obtained after PCR amplification carried out at 50° C. with the genomic DNA of the SA2 strain and of the oligonucleotides 3358 and 3357 which correspond to position 2036 and 3435 respectively on the sequence of grlA. More specifically, the sense oligonucleotide 3358 (SEQ ID No. 15) (Example 4) and the antisense oligonucleotide 3357 made it possible to amplify a fragment of 1399 base pairs; the sequence of the antisense oligonucleotide 3357 is 5'-GGCCGAGCTCCAATTCTTCTTTTATGACATTC-3' (SEQ ID No. 17). The oligonucleotide 3358 was also used to introduce, by mutagenesis, a sequence CATATG, in place of the GTG initiation codon in order to create an NdeI site. The amplified grlA fragment was cloned into the BamHI/SstI cloning sites of pUC18 (Boehringer Mannheim), and 6 clones containing this plasmid, pXL2692, were analysed after sequencing their insert. In all cases, a sequence CATATG was introduced in place of the CTG initiation codon, and the point mutation at position 2270 of grlA (C→A) was again found.

EXAMPLE 6

Expression in E. coli of the grlA gene containing a base change corresponding to the change of the residue Ser-80 to Tyr This example describes the construct prepared in order to express, in E. coli, the mutated grlA gene under the control of the T7 promoter (Studier et al., 1990). The expression plasmid pXL2742, containing the mutated grlA gene, was constructed by cloning the 0.75 kb insert of pXL2692 into the NdeI site of pXL2338 (Example 3.2). The plasmid pXL2742 was introduced into the E. coli XL1-Blue strain and the expression of the grlA gene was carried out as described in Example 3.2. The production of a protein having a molecular weight of 90,000 was obtained with the plasmid pXL2742 containing the grlA gene. The molecular weight measured is in agreement with the molecular weight deduced from the sequence of the grlA gene, and that already obtained for the wild-type GrlA protein (Example 3.2).

EXAMPLE 7

DNA topoisomerase IV activity of the GrlAB protein of S. aureus

This example illustrates how an acellular extract containing the GrlAB protein can be prepared and how the enzymatic activity of the GrlAB protein present in this extract can be detected and measured.

7.1—Preparation of the Cell Extracts

An acellular extract of the E. coli strain XL1-blue pXL2340 expressing the GrlA protein is prepared for example in the following manner: The E. coli strain XL1-blue pXL2340 is cultured as follows: 250 ml of LB medium containing ampicillin at 50 mg/l are inoculated at 1/100 with a culture of E. coli XL1-blue pXL2340, and incubated at 30° C.; when the optical density at 600 nm is 0.3, 1 mM IPTG is added; after incubating for 30 min at 37° C., the strain is infected with the helper phage M13/T7 with a multiplicity of infection of 5 pfu per cell for 4 hours. After centrifugation (5000×g; 20 min), the cells obtained using 1.5 liters of culture are resuspended in 20 ml of 50 mM Tris/HCl buffer pH 7.8 containing 10 mM EDTA, 150 mM NaCl, 1 mM DTT, 0.12% Brij 58 and 0.75 mg/ml of lysozyme. After 30 min at 4° C., the mixture is centrifuged for 1 h at 50,000×g and the supernatant containing the GrlA protein is recovered. A change of buffer is carried out on this sample by chromatographing the extract through a column filled with Sephadex G625 (Pharmacia) equilibrated and eluted with the 50 mM Tris/HCl buffer pH 7.5 containing 1 mM EDTA, 5 mM DTT, 100 mM NaCl and 10% sucrose.

An acellular extract containing the GrlB protein is prepared in a similar manner using the E. coli strain XL1-blue pXL2320.

7.2—Purification of the DNA Topoisomerase IV of S. aureus

This example illustrates how an S. aureus enzyme catalysing the segregation of the daughter chromosomes during the final phase of replication (topoisomerase IV) can be purified.

The purification of the two GrlA and GrlB subunits of topoisomerase IV is carried out as described below, using the decatenation activity assay described in Example 7.3 to detect the presence of the GrlA and GrlB proteins during the purification, as is commonly used by persons skilled in the art. During the assay of this enzymatic activity, complementation of the fractions containing the GrlA protein is obtained with 1 μg of proteins of an extract of the E. coli strain XL1-blue pXL2320 expressing the GrlB subunit, and complementation of the fraction containing the GrlB protein is obtained with 1 μg of proteins of an extract of the E. coli strain XL1-blue pXL2340 expressing the GrlA subunit. A preferred mode of preparation of the enzymatic extracts is described in Example 7.1. Between each stage, the fractions containing the desired protein are frozen and stored at −70° C. The purification of the A subunit may be carried out by chromatography, for example, according to the following procedure: an acellular extract prepared as described in Example 7.1 using about 5 g of cells of E. coli XL1-blue pXL2340 is chromatographed on a MonoQ HR 10/10 column (Pharmacia) at a flow rate of 3 ml/min with a linear gradient of NaCl (0.1M to 0.6M over 60 min) in a 10 mM Tris/HCl buffer pH 8.0 containing 1 mM EDTA, 1 mM DTT and 10% glycerol (w/v). The active fractions are combined and the sample is chromatographed on a Superdex 200 HiLoad 26/60 column (Pharmacia) equilibrated and eluted with 50 mM Tris/HCl buffer pH 7.5 containing 1 mM EDTA, 5 mM DTT and 0.25 M NaCl. The GrlA protein, which exists in the form of a symmetrical peak, is coeluted with the desired activity. After this stage, the preparation shows a single visible band in SDS-PAGE after developing with silver nitrate, and this band migrates with an apparent molecular weight of about 90,000.

The purification of the B subunit may be carried out by chromatography, for example, according to the following procedure: an acellular extract prepared as described in Example 5 using about 5 g of cells of E. coli XL1-blue pXL2320 is injected onto a Novobiocin-Sepharose CL-6B column (6 ml of gel prepared according to the procedure described by Staudenbauer et al., 1981, Nucleic Acids Research) equilibrated in 50 mM Tris/HCl buffer pH 7.5 containing 1 mM EDTA, 5 mM DTT and 0.3 M NaCl. After washing the column with the same buffer, the GrlB protein is eluted with 50 mM Tris/HCl buffer pH 7.5 containing 1 mM EDTA, 5 mM DTT and 2 M NaCl and 5 M urea. This fraction is then chromatographed on a Superdex 200 HiLoad 26/60 gel permeation column (Pharmacia) equilibrated and eluted with 50 mM Tris/HCl buffer pH 7.5 containing 1 mM EDTA, 5 mM DTT and 0.25 M NaCl. The GrlB protein, which exists in the form of a symmetrical peak, is coeluted with the desired activity. After this stage, the preparation has a single visible band in SDS-PAGE after developing with silver nitrate, and this band migrates with an apparent molecular weight of about 80,000.

7.3—Detection of the Enzymatic Activities of the GrlAB Protein

The various enzymatic activities of the GrlAB protein are detected by incubating, in the same reaction mixture, equal quantities of the two types of extracts prepared by the process described above or by any other process which makes it possible to recover the intracellular enzymatic proteins of the microorganism while preserving their activity, such as for example the procedures involving the use of presses (such as the French Press, the X-Press), or the use of ultrasound.

The ATP-dependent supercoiled DNA relaxing activity can be detected by carrying out the procedure, for example, in the following manner: a mixture of an extract of the $E.$ $coli$ strain XL1-blue pXL2320 (1 µg of proteins) and of an extract of the $E.$ $coli$ strain XL1-blue pXL2340 (1 µg of proteins) is incubated for 1 h at 37° C. in 30 µl of 50 mM Tris/HCl buffer pH 7.7 containing 4 mM ATP, 6 mM $MgCl_2$, 5 mM DTT, 1 mM spermidine, 20 mM KCl, 50 µg/ml of bovine serum albumin and 500 ng of supercoiled plasmid pBR322. The reaction is stopped by adding 7 µl of a 5% SDS and 2.5 mg/ml proteinase K mixture and the samples are incubated for a second period of 30 min at 37° C. and then analysed by electrophoresis on 1% agarose gel in 0.1 M Tris/borate buffer pH 8.3 containing 2 mM EDTA at 6 V/cm for 3 h. The separation of the relaxed and nicked (open circular) DNAs is carried out by performing an additional 2 h electrophoretic run after addition of ethidium bromide (1 µg/ml) to the running buffer. The DNA is then quantified by scanning the negatives of photographs of the gels (Polaroid type 665 film) with the aid of a Bioimage 50S apparatus (Millipore).

FIG. 4 shows that the acellular extracts of the strains $E.$ $coli$ XL1-blue pXL2320 and $E.$ $coli$ XL1-blue pXL2340 exhibit in a mixture an intense DNA relaxing activity whereas each of the extracts is inactive when it is incubated alone. The reaction is ATP-dependent. Furthermore, these two extracts, alone or in the form of a mixture, exhibit no DNA supercoiling activity, an typical of gyrase.

The ATP-dependent activity of decatenation of intertwined circular DNA molecules (catenanes) can be detected by carrying out the procedure, for example, in the following manner: a mixture of an extract of the $E.$ $coli$ strain XL1-blue pXL2320 (2.5 µg of proteins) and of an extract of the $E.$ $coli$ strain XL1-blue pXL2340 (2.5 µg of proteins) is incubated for 1 h at 37° C. in 40 µl of 50 mM Tris/HCl buffer pH 7.7 containing 1 mM ATP, 6 mM MgCl2, 200 mM glutamate, 10 mM DTT, 10 mM NaCl, 50 µg/ml of bovine serum albumin and 800 ng of kinetoplast DNA [consisting of a network of intertwined DNA molecules (catenanes) obtained from $Crithidia$ $fasciculata;$ TopoGene]. The reaction is stopped by adding 7 µl of a 250 mM EDTA solution (incubation 5 min at 37° C.), 5 µl of a 5% SDS and 2.5 mg/ml proteinase K mixture (incubation 30 min at 37° C.). The mixture is then analysed by electrophoresis on a 1% agarose gel in a 0.1 M Tris/borate buffer pH 8.3 containing 2 mM EDTA at 6 V/cm for 2 h 30 min. After staining the DNA with ethidium bromide (1 µg/ml), the DNA is quantified by scanning the negatives of photographs of the gels (Polaroid type 665 film) with the aid of a Bioimage 50S apparatus (Millipore). By working, for example, under the conditions described above, the extracts of the two strains $E.$ $coli$ XL1-blue pXL2320 and $E.$ $coli$ XL1-blue pXL2340 exhibit, in the form of a mixture, an activity of complete decatenation of the starting kinetoplast DNA. This activity is detected by the appearance of a DNA band with a size of about 2.5 kb and by the disappearance of the band of catenated DNA of very large size which penetrates very little into the gel during the electrophoretic run (FIG. 5). The $E.$ $coli$ gyrase introduced as a control into this assay exhibits no decatenation activity contrary to DNA topoisomerase IV of $E.$ $coli$ which completely decatanates the kinetoplast DNA (FIG. 5).

EXAMPLE 8

DNA topoisomerase IV activity of the GrlAB protein of $S.$ $aureus$ whose GrlA subunit exhibits a substitution of the residue Ser-80 to Tyr (Ser-80→Tyr)

8.1—Preparation of a cell extract containing the GrlAB protein of $S.$ $aureus$ whose GrlA subunit exhibits a substitution of the residue Ser-80 to Tyr (Ser-80→Tyr)

This example illustrates how an acellular extract containing the protein GrlA(Ser-80→Tyr)B can be prepared, and how the enzymatic activity of the protein GrlA(Ser-80→Tyr)B can be detected and measured.

An acellular extract of the $E.$ $coli$ strain XL1-Blue pXL2742 expressing the protein GrlA(Ser-80→Tyr) is prepared, for example, as described in Example 7 for the wild-type GrlA protein.

8.2—Purification of a DNA topoisomerase IV of $S.$ $aureus$ exhibiting an Ser-80-Tyr mutation in the GrlA subunit This example illustrates how a topoisomerase IV of $S.$ $aureus$ exhibiting an Ser-80→Tyr mutation in the GrlA subunit can be purified. The GrlA subunit of topoisomerase IV having an Ser-80→Tyr mutation is purified according to a procedure identical to that described in Example 7.2 using a culture of the $E.$ $coli$ strain XL1-blue pXL2742 constructed as described in Example 6.

8.3—Detection of the enzymatic activities

The ATP-dependent activities of supercoiled DNA relaxation, on the one hand, and of decatenation of intertwined circular DNA molecules, on the other hand, are detected in this extract as described in Example 7, by incubating, in the same reaction mixture, an acellular extract of the $E.$ $coli$ strain XL1-Blue pXL2742 containing the protein GrlA(Ser-80→Tyr) and an extract of the $E.$ $coli$ strain XL1-Blue pXL2320 containing the GrlB protein.

EXAMPLE 9

Inhibition by fluoroquinolones, of the DNA topoisomerase IV activity of the wild-type GrlAB protein of $S.$ $aureus$ and resistance to fluoroquinolones of the protein containing an Ser-80→Tyr transistion in the GrlA subunit The two methods described in Example 7 for the assay of DNA topoisomerase IV activities can be used to detect novel molecules which act as inhibitors of topoisomerase IV of $S.$

*aureus* or the characterize the behaviour of topoisomerase IV of *S. aureus* towards molecules already identified as inhibitors of other topoisomerases (for example the fluoroquinolones).

In the test of relaxation of supercoiled DNA for example, the disappearance or the decrease in the relaxed DNA band during analysis of the reaction mixture after incubation of the GrlAB protein of *S. aureus* in the presence of a molecule or of a mixture of several molecules indicates that this molecule (or these molecules), inhibit the relaxation activity of GrlAB, and is therefore potentially antibacterial. However, since the studies carried out up until now (described in Example 7) have demonstrated that the GrlAB protein is a topoisomerase IV, and since it is nowadays established that the major function of the topoisomerases IV is decatenation (or disentanglement) of the intertwined daughter chromosomes during the final stages of replication, it seems more judicious to search for the inhibitors of the GrlAB protein using a test of decatenation of DNA using, for example, the test described in Example 7.3. To carry out the experiments described in the examples which follow, the incubations are carried out with the purified wild-type GrlAB proteins as described in Example 7, and with the mutant protein GrlA(Ser-80→Tyr)B as described in Example 8. The two wild-type and mutant GrlAB proteins are reconstituted by mixing equimolar quantities of their two GrlA and GrlB subunits.

In the decatenation test, if the disappearance or the decrease in the intensity of the decatenated DNA band is observed during analysis of the reaction mixture after incubation of the GrlAB protein in the presence of a molecule or of a mixture of several molecules, this indicates that this molecule (or these molecules) inhibits the decatenation activity of the GrlAB protein, and is therefore potentially antibacterial. Since it has been demonstrated in the present invention that the GrlAB protein is the primary target for the molecules of the fluoroquinolone family, it appears that the fluoroquinolones must act as inhibitors in the decatenation test described in Example 7. Indeed, when the purified GrlAB protein is incubated in the presence of increasing quantities of a fluoroquinolone, for example ciprofloxacin, it appears that above a concentration of 10 µg/ml, ciprofloxacin completely inhibits the activity of decatenation of the kinetoplast DNA. Ciprofloxacin inhibits 50% of the activity of decatenation of kinetoplast DNA at a concentration of 4.0 µg/ml.

Likewise, sparfloxacin which is another fluoroquinolone inhibits 50% of the activity of decatenation of kinetoplast DNA at a concentration of 6.0 µg/ml.

Likewise, since it has been demonstrated in the present invention (Example 4) that the presence of an Ser-80→Tyr mutation on the GrlA subunit of the mutant GrlAB protein confers on the strain a certain level of resistance to fluoroquinolones, for example ciprofloxacin, it appears that the fluoroquinolones must act on this mutant DNA topoisomerase IV as inhibitors which are less efficient in the decatenation test described in Example 7.

Indeed, when the mutant protein GrlA(Ser-80→Tyr)B is incubated in the presence of increasing quantities of a fluoroquinolone, for example ciprofloxacin, it appears that ciprofloxacin inhibits 50% of the activity of decatenation of kinetoplast DNA at a concentration of 60 µg/ml, that is to say a concentration 15 times as high as that necessary to obtain the same effect with the wild-type enzyme.

Likewise, in the presence of the mutant enzyme GrlA (Ser-80→Tyr)B, sparfloxacin inhibits 50% of the activity of decatenation of kinetoplast DNA at a concentration of 500 µg/ml, that is to say a concentration 80 times as high as that necessary to obtain the same effect with the wild-type enzyme.

Norfloxacin inhibits 50% of the activity of decatenation of kinetoplast DNA at a concentration of 12 µg/ml with the wild-type GrlAB enzyme and exhibits the same inhibitory activity at a concentration of 125 µg/ml with the enzyme GrlA(Ser-80→Tyr)B. Ofloxacin inhibits 50% of the activity of decatenation of kinetoplast DNA at a concentration of 10 µg/ml with the wild-type GrlAB enzyme and has the same inhibitory activity at a concentration of 250 µg/ml with the enzyme GrlA(Ser-80→Tyr)B.

Novobiocin, whose mechanism of action is different from that of the fluoroquinolones, should therefore in principle have the same inhibitory activity on both the wild-type GrlAB enzyme and on the mutant GrlA(Ser-80→Tyr)B enzyme in the decatenation test described in Example 7. Indeed, novobiocin inhibits 50% of the activity of decatenation of kinetoplast DNA at a concentration of about 30 µg/ml whatever the enzyme used (wild-type GrlAB or mutant GrlA(Ser-80→Tyr)).

ABBREVIATIONS

DNA: deoxyribonucleic acid
RNA: ribonucleic acid
MIC: minimum inhibitory concentration
IPTG: isopropylthio-β-D-galactoside
LB: Luria-Bertani medium
PAGE: electrophoresis gel containing acrylamide and N,N'-methylenebisacrylamide
PCR: polymerase chain reaction
pfu: plaque forming unit
QRDR: region of the GyrA subunit where the point mutations leading to resistance to fluoroquinolones are mapped
SDS: sodium dodecyl sulphate
Tris: tris(hydroxymethyl)aminomethane

REFERENCES

Adachi, T., Mizuuchi, M., Robinson, E. A., Apella, E., O'Dea, M. H., Gellert, M., and Mizuuchi K. (1987) DNA sequence of the *E. coli* gyrB gene: application of a new sequencing strategy. *Nucl Acid Res* 15: 771–784.

Bagdasarian, M., Lurz, R., Rückert, B., Franklin, F. C., Bagdasarian, M. M., Frey, J., and Timmis, K. (1981) Specific-purpose plasmid cloning vectors. II. Broad host range, high copy number, RSF1010-derived vectors, and a host-vector system for gene cloning in Pseudomonas. *Gene* 16: 237–247.

Colman, S. D., Hu, P. C., and Bott, K. F. (1990) *Mycoplasma pneumoniae* DNA gyrase genes. *Mol Microbiol* 4: 1129–11134.

Cullen, M. E., Wyke, A. W., Kuroda, R., and Fisher, L. M. (1989) Cloning and characterization of a DNA gyrase gene from *Escherichia coli* that confers clinical resistance to 4-quinolones *Antimicrob Agents Chemother* 33: 886–894.

Denèfle, P., Kovarik, S., Guiton, J. D., Cartwright, T., and Mayaux, J.-F. (1987) Chemical synthesis of a gene coding for human angiogenin, its expression in *Escherichia coli* and conversion of the product into its active form. *Gene* 56: 61–70.

Gellert, M., Mizuuchi, K., O'Dea, M. H. and Nash, H. A. (1976) DNA gyrase: an enzyme that introduces superhelical turns into DNA *Proc Natl Acad Sci USA* 73: 3872–3876.

Goswitch, J. J., Willard, K. E., Fasching, C. E., and Peterson, L. R. (1992) Detection of gyrA gene mutations associated with ciprofloxacin resistance in methicillin-resistant *Staphylococcus aureus*: analysis by polymerase chain reaction and automated direct DNA sequencing. *Antimicrob Agents Chemother* 36: 1166–1169.

Higgins, D. G., and Sharp, P. M. (1988) Clustal: a package for performing multiple sequence alignment on a microcomputer. *Gene* 73: 237–244.

Holmes, M. L., and Dyall-Smith, M. (1991) Mutations in the DNA gyrase result in novobiocin resistance in halophilic archaebacteria. *J Bacteriol* 173: 642–648.

Hooper, D. C., Wolfson, J. S. (1993) Mechanisms of quinolone action and bacterial killing. In Quinolone Antimicrobial Agents. Hooper, D. C., Wolfson, J. S. (eds) Washington: American Society of Microbiology, pp. 53–75.

Horowitz, D. S., and Wang, J. C. (1987) Mapping of the active site tyrosine of *Escherichia coli* DNA gyrase. *J Biol Chem* 262: 5339–5344.

Huang, W. M. (1992) Multiple DNA gyrase-like genes in Eubacteria. In *Molecular Biology of DNA Topoisomerases and its Application to Chemotherapy*. Andoh, T., Ikeda, H., and Oguro, M. (eds). London: CRC Press, pp. 39–48.

Kanehisa, M. (1984) Use of statistical criteria for screening potential homologies in nucleic acids sequences. *Nucl Acids Res* 12: 203–215.

Kato, J., Suzuki, H., and Ikeda, E. (1992) Purification and characterization of DNA topoisomerase-IV in *Escherichia coli*. *J Biol Chem* 267: 25676–25684.

Kato, J., Nishimura, Y., Imamura, R., Niki, H., Higara, S., and Suzuki, H. (1990) New topoisomerase essential for chromosome segregation in *E. coli*. *Cell* 63: 393–404.

Luttinger, A. L., Springer, A. L., and Schmid, M. B. (1991) A cluster of genes that affects nucleoid segregation in *Salmonella typhimurium*. *New Biol* 3: 687–697.

Margerrison, E. E. C., Hopewell, R. and L. M. Fisher. (1992) Nucleotide sequence of the *Staphylococcus aureus* gyrB-gyrA locus encoding the DNA gyrase A and B proteins. *J Bacteriol* 174: 1596–1603.

Maxwell, A. (1992) The molecular basis of quinolone action. *J. Antimicrob. Chemother.* 330: 409–416.

Moriya, S., Ogasawara, N. and Yoshida, H. (1985) Structure and function of the region of the replication origin of *Bacillus subtilis* chromosome. III. Nucleotide sequence of some 10,000 base pairs in the origin region. *Nucl Acid Res* 13: 2251–2265.

Normark, S., Bergtröm, S., Edlund, T., Grundström, T., Jaurin, B., Lindberg, F., and Olsson, O. (1983) Overlapping genes. *Ann Rev Genet* 17: 499–525.

Novick, R. P. (1990) The staphylococcus as a molecular genetic system. In *Molecular Biology of the Staphylococci*. Novick, R. P. (ed). New York: VCH Publishers, pp. 1–37.

Parales, R. E., and Harwood, C. S. (1990) Nucleotide sequence of the gyrB gene of *Pseudomonas putida*. *Nucl Acid Res* 18: 5880–5880.

Peng, H., Marians, K. J. (1993 (a)) *Escherichia coli* topoisomerase IV Purification, charcterization, subunit structure, and subunit interactions. *J Biol Chem* 268: 24481–24490.

Peng, H., Marians, K. J. (1993 (b)) Decatenation activity of topoisomerase IV during oriC and pBR322 DNA replication in vitro. *Proc Natl Acad Sci USA* 90: 8571–8575.

Sambrook J., Fritsch, E. F., and Maniatis, T. (1989) Molecular Cloning: a Laboratory Manual 2nd edn. Cold Spring Harbor, N.Y.: Cold Spring Harbor Laboratory Press.

Streedharan, S., Peterson, L., and Fisher, L. M. (1991) Ciprofloxacin-resistance in coagulase-positive and -negative Straphylococci: role of mutations at serine 84 in the DNA gyrase A protein of *Staphylococcus aureus:* and *Staphylococcus epidermidis Antimicrob Agents Chemother* 35: 2151–2154.

Sreedharan, S., Oram, M., Jensen, B., Peterson, L., and Fisher, L. M. (1990) DNA gyrase gyrA mutations in ciprofloxacin-resistant strains of *Staphylococcus aureus:* close similarity with quinolone resistance mutations in *Escherichia coli*. *J Bacteriol* 172: 7260–7262.

Staden, R., and McLachlan, A. D. (1982) Codon preference and its use in identifying protein coding regions in long DNA sequences. *Nucl Acid Res* 10: 141–156.

Staudenbauer, W. L., and Orr, E. (1981) DNA gyrase: affinity chromatography on novobiocin-Sepharose and catalytic properties *Nucleic Acid Research* 9: 3589–3603

Stein, D. C., Danaher, R. J., and Cook, T. M. (1991) Characterization of a gyrB mutation responsible for low-level nalidixic acid resistance in *Neisseria gonorrhoeae*. *Antimicrob Agents Chemother* 35: 622–626.

Studier, W. F., Rosenberg, A. H., Dunn, J. J., and Duberndorff, J. W. (1990) Use of T7 RNA polymerase to direct expression of cloned genes. *Methods Enzymol*. 185: 89–60.

Swamberg, S. L. and Wang, J. C. (1987) Cloning and sequencing of the *Escherichia coli* Dan gyrA gene coding for the A subunit of DNA gyrase. *J Mol Biol* 197: 729–736.

Thiara, A. M., and Cundliffe, E. (1993) Expression and analysis of two gyrB genes from the novobiocin producer, *Streptomyces sphaeroides*. *Mol Microbiol* 8: 495–506.

Wang, J. C., and Liu, L. F. (1990) DNA replication: topological aspect and the roles of DNA topoisomerases. In *DNA Topology and its Biological Effects*. Cozzarelli, N. R., and Wang, J. C. (eds). New York: Cold Spring Harbor Laboratory Press, pp. 321–340.

Wang, Y., Huange, W. M. and Taylor, D. E. (1993) Cloning and nucleotide sequence of the *Campylobacter jejuni* gyrA gene and characterization of quinolone resistance mutations. *Antimicrob Agents and Chemother* 37: 457–463.

Wigley, D. B., Davies, G. J., Dobson, E. J., Maxwell, A., and Dodson, G. (1991) Crystal structure of an $NH_2$-terminal fragment of the DNA gyrase B protein. *Nature* 351: 624–629.

Yoshida, H., Bogaki, M., Nakamura, M., and Nakamura, S. (1990) Quinolone resistance determining region in the DNA gyrase gene of *Escherichia coli*. *Antimicrob Agents Chemother* 34: 1271–1272.

What is claimed is:

1. An isolated polypeptide resulting from the expression of a nucleotide sequence chosen from:
   (a) all or a part of the gr1A gene (SEQ ID NO:4) or all or a part of the gr1B gene (SEQ ID NO:6); or
   (b) sequences derived from the sequences of (a) because of the degeneracy of the genetic code,
      wherein the polypeptide expressed from all or a part of the gr1A gene exhibits topoisomerase activity in the presence of a Gr1B subunit and
      wherein the polypeptide expressed from all or a part of the gr1B gene exhibits topoisomerase activity in the presence of a Gr1A subunit.

2. An isolated polypeptide according to claim 1, characterized in that it is the polypeptide Gr1A (SEQ ID NO:3).

3. An isolated polypeptide according to claim 1, characterized in that it is the polypeptide Gr1B (SEQ ID NO:5).

4. An isolated polypeptide comprising SEQ ID NO:3, wherein the serine at amino acid position 80 has been changed to a tyrosine.

5. An isolated topoisomerase IV characterized in that it is capable of being obtained from the expression of a nucleotide sequence chosen from:
   (a) all or a part of the gr1A gene (SEQ ID NO:4) or all or a part of the gr1B gene (SEQ ID NO:6); or
   (b) sequences derived from the sequences of (a) because of the degeneracy of the genetic code,
      wherein the polypeptide expressed from all or a part of the gr1A gene exhibits topoisomerase activity in the presence of a Gr1B subunit and
      wherein the polypeptide expressed from all or a part of the gr1B gene exhibits topoisomerase activity in the presence of a Gr1A subunit.

6. An isolated topoisomerase according to claim 5, characterized in that it is capable of being obtained from the expression of a nucleotide sequence comprising all or a part of the gr1A gene (SEQ ID NO:4) and all or a part of the gr1B gene (SEQ ID NO:6).

7. An isolated topoisomerase IV according to claim 5, characterized in that it is a primary target of the fluoroquinolones.

8. An isolated topoisomerase IV according to claim 5, characterized in that it is topoisomerase IV of *Staphylococcus aureus*.

* * * * *

SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
    (A) LENGTH: 4565 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 1:

```
GAATTCCGAC GTACGTTTGC AGGAGGCGAA ATCATTGGCA ATGAATAAAC AAAATAATTA    60
TTCAGATGAT TCAATACAGG TTTTAGAGGG GTTAGAAGCA GTTCGTAAAA GACCTGGTAT   120
GTATATTGGA TCAACTGATA ACGGGGATT ACATCATCTA GTATATGAAA TTGTCGATAA    180
CTCCGTCGAT GAAGTATTGA ATGGTTACGG TAACGAAATA GATGTAACAA TTAATAAAGA   240
TGGTAGTATT TCTATAGAAG ATAATGGACG TGGTATGCCA ACAGGTATAC ATAAATCAGG   300
TAAACCGACA GTCGAAGTTA TCTTTACTGT TTTACATGCA GGAGGTAAAT TTGGACAAGG   360
TGGCTATAAA ACTTCAGGTG GTCTTCACGG CGTTGGTGCT TCAGTGGTAA ATGCATTGAG   420
TGAATGGCTT GAAGTTGAAA TCCATCGAGA TGGTAATATA TATCATCAAA GTTTTAAAAA   480
CGGTGGTTCG CCATCTTCAG GTTTAGTGAA AAAAGGTAAA ACTAAGAAAA CAGGTACCAA   540
AGTAACATTT AAACCTGATG ACACAATTTT TAAAGCATCT ACATCATTTA ATTTTGATGT   600
TTTAAGTGAA CGACTACAAG AGTCTGCGTT CTTATTGAAA AATTTAAAAA TAACGCTTAA   660
TGATTTACGC AGTGGTAAAG AGCGTCAAGA GCATTACCAT TATGAAGAAG GAATCAAAGA   720
GTTTGTTAGT TATGTCAATG AAGGAAAAGA AGTTTTGCAT GACGTGGCTA CATTTTCAGG   780
TGAAGCAAAT GGTATAGAGG TAGACGTAGC TTTCCAATAT AATGATCAAT ATTCAGAAAG   840
TATTTTAAGT TTTGTAAATA ATGTACGTAC TAAAGATGGT GGTACACATG AAGTTGGTTT   900
TAAAACAGCA ATGACACGCG TATTTAATGA TTATGCACGT CGTATTAATG AACTTAAAAC   960
AAAAGATAAA AACTTAGATG GTAATGATAT TCGTGAAGGT TTAACAGCTG TTGTGTCTGT  1020
TCGTATTCCA GAAGAATTAT TGCAATTTGA AGGACAAACG AAATCTAAAT TGGGTACTTC  1080
TGAAGCTAGA AGTGCTGTTG ATTCAGTTGT TGCAGACAAA TTGCCATTCT ATTTAGAAGA  1140
AAAAGGACAA TTGTCTAAAT CACTTGTGAA AAAAGCGATT AAAGCACAAC AAGCAAGGGA  1200
AGCTGCACGT AAAGCTCGTG AAGATGCTCG TTCAGGTAAG AAAAACAAGC GTAAAGACAC  1260
TTTGCTATCT GGTAAATTAA CACCTGCACA AAGTAAAAAC ACTGAAAAAA ATGAATTGTA  1320
TTTAGTCGAA GGTGATTCTG CGGGAGGTTC AGCAAAACTT GGACGAGACC GCAAATTCCA  1380
AGCGATATTA CCATTACGTG GTAAGGTAAT TAATACAGAG AAAGCACGTC TAGAAGATAT  1440
TTTTAAAAAT GAAGAAATTA ATACAATTAT CCACACAATC GGGGCAGGCG TTGGTACTGA  1500
CTTTAAAATT GAAGATAGTA ATTATAATCG TGTAATTATT ATGACTGATG CTGATACTGA  1560
TGGTGCGCAT ATTCAAGTGC TATTGTTAAC ATTCTTCTTC AAATATATGA AACCGCTTGT  1620
TCAAGCAGGT CGTGTATTTA TTGCTTTACC TCCACTTTAT AAATTGGAAA AAGGTAAAGG  1680
CAAAACAAAG CGAGTTGAAT ACGCTTGGAC AGACGAAGAG CTTAATAAAT TGCAAAAAGA  1740
ACTTGGTAAA GGCTTCACGT TACAACGTTA CAAAGGTTTG GGTGAAATGA ACCCTGAACA  1800
ATTATGGGAA ACGACGATGA ACCCAGAAAC ACGAACTTTA ATTCGTGTAC AAGTTGAAGA  1860
TGAAGTGCGT TCATCTAAAC GTGTAACAAC ATTAATGGGT GACAAAGTAC AACCTAGACG  1920
TGAATGGATT GAAAAGCATG TTGAGTTTGG TATGCAAGAG GACCAAAGTA TTTTAGATAA  1980
TTCTGAAGTA CAAGTGCTTG AAAATGATCA ATTTGATGAG GAGGAAATCT AGTGAGTGAA  2040
ATAATTCAAG ATTTATCACT TGAAGATGTT TTAGGTGATC GCTTTGGAAG ATATAGTAAA  2100
```

```
TATATTATTC AAGAGCGTGC ATTGCCAGAT GTTCGTGATG GTTTAAAACC AGTACAACGT   2160

CGTATTTTAT ACGCAATGTA TTCAAGTGGT AATACACACG ATAAAAATTT CCGTAAAAGT   2220

GCGAAAACAG TCGGTGATGT TATTGGTCAA TATCATCCAC ATGGAGACTC CTCAGTGTAC   2280

GAAGCAATGG TCCGTTTAAG TCAAGACTGG AAGTTACGAC ATGTCTTAAT AGAAATGCAT   2340

GGTAATAATG GTAGTATCGA TAATGATCCG CCAGCGGCAA TGCGTTACAC TGAAGCTAAG   2400

TTAAGCTTAC TAGCTGAAGA GTTATTACGT GATATTAATA AGAGACAGT TTCTTTCATT    2460

CCAAACTATG ATGATACGAC ACTCGAACCA ATGGTATTGC CATCAAGATT TCCTAACTTA   2520

CTAGTGAATG GTTCTACAGG TATATCTGCA GGTTACGCGA CAGATATACC ACCACATAAT   2580

TTAGCTGAAG TGATTCAAGC AACACTTAAA TATATTGATA ATCCGGATAT TACAGTCAAT   2640

CAATTAATGA AATATATTAA AGGTCCTGAT TTTCCAACTG GTGGTATTAT TCAAGGTATT   2700

GATGGTATTA AAAAAGCTTA TGAATCAGGT AAAGGTAGAA TTATAGTTCG TTCTAAAGTT   2760

GAAGAAGAAA CTTTACGCAA TGGACGTAAA CAGTTAATTA TTACTGAAAT TCCATATGAA   2820

GTGAACAAAG GTAGCTTAGT AAAACGTATC GATGAATTAC GTGCTGACAA AAAGTCGAT    2880

GGTATCGTTG AAGTACGTGA TGAAACTGAT AGAACTGGTT TACGAATAGC AATTGAATTG   2940

AAAAAAGATG TGAACAGTGA ATCAATCAAA AATTATCTTT ATAAAAACTC TGATTTACAG   3000

ATTTCATATA ATTTCAACAT GGTCGCTATT AGTGATGGTC GTCCAAAATT GATGGGTATT   3060

CGTCAAATTA TAGATAGTTA TTTGAATCAT CAAATTGAGG TTGTTGCAAA TAGAACGAAG   3120

TTTGAATTAG ATAATGCTGA AAAACGTATG CATATCGTTG AAGGTTTGAT TAAAGCGTTG   3180

TCAATTTTAG ATAAAGTAAT CGAATTGATT CGTAGCTCTA AAAACAAGCG TGACGCTAAA   3240

GAAAACCTTA TCGAAGTATA CGAGTTCACA GAAGAACAGG CTGAAGCAAT TGTAATGTTA   3300

CAGTTATATC GTTAACAAA CACTGACATA GTTGCGCTTG AAGGTGAACA TAAAGAACTT    3360

GAAGCATTAA TCAAACAATT ACGTCATATT CTTGATAACC ATGATGCATT ATTGAATGTC   3420

ATAAAAGAAG AATTGAATGA AATTAAAAAG AAATTCAAAT CTGAACGACT GTCTTTAATT   3480

GAAGCAGAAA TTGAAGAAAT TAAAATTGAC AAAGAAGTTA TGGTGCCTAG TGAAGAAGTT   3540

ATTTTAAGTA TGACACGTCA TGGATATATT AAACGTACTT CTATTCGTAG CTTTAATGCT   3600

AGCGGTGTTG AAGATATTGG TTTAAAAGAT GGTGACAGTT TACTTAAACA TCAAGAAGTA   3660

AATACGCAAG ATACCGTACT AGTATTTACA AATAAAGGTC GTTATCTATT TATACCAGTT   3720

CATAAATTAC GAGATATTCG TTGGAAAGAA TTGGGGCAAC ATGTATCACA AATAGTTCCT   3780

ATCGAAGAAG ATGAAGTGGT TATTAATGTC TATAATGAAA AGGACTTTAA TACTGATGCA   3840

TTTTATGTTT TTGCGACTCA AAATGGCATG ATTAAGAAAA GTACAGTGCC TCTATTTAAA   3900

ACAACGCGTT TTAATAAACC TTTAATTGCA ACTAAAGTTA AGAAAATGA TGATTTGATT    3960

AGTGTTATGC GCTTTGAAAA AGATCAATTA ATTACCGTAA TTACAAATAA AGGTATGTCA   4020

TTAACGTATA ATACAAGTGA ACTATCAGAT ACTGGATTAA GGGCGGCTGG TGTTAAATCA   4080

ATAAATCTTA AAGTTGAAGA TTTCGTTGTT ATGACAGAAG GTGTTTCTGA AAATGATACT   4140

ATATTGATGG CCACACAACG CGGCTCGTTA AAACGTATTA GTTTTAAAAT CTTACAAGTT   4200

GCTAAAAGAG CACAACGTGG AATAACTTTA TTAAAAGAAT TAAAGAAAAA TCCACATCGT   4260

ATAGTAGCTG CACATGTAGT GACAGGTGAA CATAGTCAAT ATACATTATA TTCAAAATCA   4320

AACGAAGAAC ATGGTTTAAT TAATGATATT CATAAATCTG AACAATATAC AAATGGCTCA   4380

TTCATTGTAG ATACAGATGA TTTTGGTGAA GTAATAGACA TGTATATTAG CTAAAAACTA   4440
```

```
TATGCAATCA CGAAATTAAA TGATAAAATA CAGTAATGTT AAATTTTGAC TAAATTCAAG    4500

GGATTTATAT TAAATGCTGA CCAAGTACTT ATCGTTAAAT TAGCGATACG GAATCCGCGG    4560

AATTC                                                                4565
```

(2) INFORMATION FOR SEQ ID NO: 2:

(i) SEQUENCE CHARACTERISTICS:
        (A) LENGTH: 4565 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 2:

```
CTTAAGGCTG CATGCAAACG TCCTCCGCTT TAGTAACCGT TACTTATTTG TTTTATTAAT      60

AAGTCTACTA AGTTATGTCC AAAATCTCCC CAATCTTCGT CAAGCATTTT CTGGACCATA     120

CATATAACCT AGTTGACTAT TTGCCCCTAA TGTAGTAGAT CATATACTTT AACAGCTATT     180

GAGGCAGCTA CTTCATAACT TACCAATGCC ATTGCTTTAT CTACATTGTT AATTATTTCT     240

ACCATCATAA AGATATCTTC TATTACCTGC ACCATACGGT TGTCCATATG TATTTAGTCC     300

ATTTGGCTGT CAGCTTCAAT AGAAATGACA AAATGTACGT CCTCCATTTA AACCTGTTCC     360

ACCGATATTT TGAAGTCCAC CAGAAGTGCC GCAACCACGA AGTCACCATT TACGTAACTC     420

ACTTACCGAA CTTCAACTTT AGGTAGCTCT ACCATTATAT ATAGTAGTTT CAAAATTTTT     480

GCCACCAAGC GGTAGAAGTC CAAATCACTT TTTTCCATTT TGATTCTTTT GTCCATGGTT     540

TCATTGTAAA TTTGGACTAC TGTGTTAAAA ATTTCGTAGA TGTAGTAAAT TAAAACTACA     600

AAATTCACTT GCTGATGTTC TCAGACGCAA GAATAACTTT TTAAATTTTT ATTGCGAATT     660

ACTAAATGCG TCACCATTTC TCGCAGTTCT CGTAATGGTA ATACTTCTTC CTTAGTTTCT     720

CAAACAATCA ATACAGTTAC TTCCTTTTCT TCAAAACGTA CTGCACCGAT GTAAAAGTCC     780

ACTTCGTTTA CCATATCTCC ATCTGCATCG AAAGGTTATA TTACTAGTTA TAAGTCTTTC     840

ATAAAATTCA AAACATTTAT TACATGCATG ATTTCTACCA CCATGTGTAC TTCAACCAAA     900

ATTTTGTCGT TACTGTGCGC ATAAAATTACT AATACGTGCA GCATAATTAC TTGAATTTTG    960

TTTTCTATTT TTGAATCTAC CATTACTATA AGCACTTCCA AATTGTCGAC AACACAGACA    1020

AGCATAAGGT CTTCTTAATA ACGTTAAACT TCCTGTTTGC TTTAGATTTA ACCCATGAAG    1080

ACTTCGATCT TCACGACAAC TAAGTCAACA ACGTCTGTTT AACGGTAAGA TAAATCTTCT    1140

TTTTCCTGTT AACAGATTTA GTGAACACTT TTTTCGCTAA TTTCGTGTTG TTCGTTCCCT    1200

TCGACGTGCA TTTCGAGCAC TTCTACGAGC AAGTCCATTC TTTTTGTTCG CATTTCTGTG    1260

AAACGATAGA CCATTTAATT GTGGACGTGT TTCATTTTTG TGACTTTTTT TACTTAACAT    1320

AAATCAGCTT CCACTAAGAC GCCCTCCAAG TCGTTTTGAA CCTGCTCTGG CGTTTAAGGT    1380

TCGCTATAAT GGTAATGCAC CATTCCATTA ATTATGTCTC TTTCGTGCAG ATCTTCTATA    1440

AAAATTTTTA CTTCTTTAAT TATGTTAATA GGTGTGTTAG CCCCGTCCGC AACCATGACT    1500

GAAATTTTAA CTTCTATCAT TAATATTAGC ACATTAATAA TACTGACTAC GACTATGACT    1560

ACCACGCGTA TAAGTTCACG ATAACAATTG TAAGAAGAAG TTTATATACT TTGGCGAACA    1620

AGTTCGTCCA GCACATAAAT AACGAAATGG AGGTGAAATA TTTAACCTTT TTCCATTTCC    1680

GTTTTGTTTC GCTCAACTTA TGCGAACCTG TCTGCTTCTC GAATTATTTA ACGTTTTTCT    1740

TGAACCATTT CCGAAGTGCA ATGTTGCAAT GTTTCCAAAC CCACTTTACT TGGGACTTGT    1800
```

-continued

```
TAATACCCTT TGCTGCTACT TGGGTCTTTG TGCTTGAAAT TAAGCACATG TTCAACTTCT      1860

ACTTCACGCA AGTAGATTTG CACATTGTTG TAATTACCCA CTGTTTCATG TTGGATCTGC      1920

ACTTACCTAA CTTTTCGTAC AACTCAAACC ATACGTTCTC CTGGTTTCAT AAAATCTATT      1980

AAGACTTCAT GTTCACGAAC TTTTACTAGT TAAACTACTC CTCCTTTAGA TCACTCACTT      2040

TATTAAGTTC TAAATAGTGA ACTTCTACAA AATCCACTAG CGAAACCTTC TATATCATTT      2100

ATATAATAAG TTCTCGCACG TAACGGTCTA CAAGCACTAC CAAATTTTGG TCATGTTGCA      2160

GCATAAAATA TGCGTTACAT AAGTTCACCA TTATGTGTGC TATTTTTAAA GGCATTTTCA      2220

CGCTTTTGTC AGCCACTACA ATAACCAGTT ATAGTAGGTG TACCTCTGAG GAGTCACATG      2280

CTTCGTTACC AGGCAAATTC AGTTCTGACC TTCAATGCTG TACAGAATTA TCTTTACGTA      2340

CCATTATTAC CATCATAGCT ATTACTAGGC GGTCGCCGTT ACGCAATGTG ACTTCGATTC      2400

AATTCGAATG ATCGACTTCT CAATAATGCA CTATAATTAT TTCTCTGTCA AAGAAAGTAA      2460

GGTTTGATAC TACTATGCTG TGAGCTTGGT TACCATAACG GTAGTTCTAA AGGATTGAAT      2520

GATCACTTAC CAAGATGTCC ATATAGACGT CCAATGCGCT GTCTATATGG TGGTGTATTA      2580

AATCGACTTC ACTAAGTTCG TTGTGAATTT ATATAACTAT TAGGCATATA ATGTCAGTTA      2640

GTTAATTACT TTATATAATT TCCAGGACTA AAAGGTTGAC CACCATAATA AGTTCCATAA      2700

CTACCATAAT TTTTTCGAAT ACTTAGTCCA TTTCCATCTT AATATCAAGC AAGATTTCAA      2760

CTTCTTCTTT GAAATGCGTT ACCTGCATTT GTCAATTAAT AATGACTTTA AGGTATACTT      2820

CACTTGTTTC CATCGAATCA TTTTGCATAG CTACTTAATG CACGACTGTT TTTTCAGCTA      2880

CCATAGCAAC TTCATGCACT ACTTTGACTA TCTTGACCAA ATGCTTATCG TTAACTTAAC      2940

TTTTTTCTAC ACTTGTCACT TAGTTAGTTT TTAATAGAAA TATTTTTGAG ACTAAATGTC      3000

TAAAGTATAT TAAAGTTGTA CCAGCGATAA TCACTACCAG CAGGTTTTAA CTACCCATAA      3060

GCAGTTTAAT ATCTATCAAT AAACTTAGTA GTTTAACTCC AACAACGTTT ATCTTGCTTC      3120

AAACTTAATC TATTACGACT TTTTGCATAC GTATAGCAAC TTCCAAACTA ATTTCGCAAC      3180

AGTTAAAATC TATTTCATTA GCTTAACTAA GCATCGAGAT TTTTGTTCGC ACTGCGATTT      3240

CTTTTGGAAT AGCTTCATAT GCTCAAGTGT CTTCTTGTCC GACTTCGTTA ACATTACAAT      3300

GTCAATATAG CAAATTGTTT GTGACTGTAT CAACGCGAAC TTCCACTTGT ATTTCTTGAA      3360

CTTCGTAATT AGTTTGTTAA TGCAGTATAA GAACTATTGG TACTACGTAA TAACTTACAG      3420

TATTTTCTTC TTAACTTACT TTAATTTTTC TTTAAGTTTA GACTTGCTGA CAGAAATTAA      3480

CTTCGTCTTT AACTTCTTTA ATTTAACTG TTTCTTCAAT ACCACGGATC ACTTCTTCAA      3540

TAAAATTCAT ACTGTGCAGT ACCTATATAA TTTGCATGAA GATAAGCATC GAAATTACGA      3600

TCGCCACAAC TTCTATAACC AAATTTTCTA CCACTGTCAA ATGAATTTGT AGTTCTTCAT      3660

TTATGCGTTC TATGGCATGA TCATAAATGT TTATTTCCAG CAATAGATAA ATATGGTCAA      3720

GTATTTAATG CTCTATAAGC AACCTTTCTT AACCCCGTTG TACATAGTGT TTATCAAGGA      3780

TAGCTTCTTC TACTTCACCA ATAATTACAG ATATTACTTT TCCTGAAATT ATGACTACGT      3840

AAAATACAAA AACGCTGAGT TTTACCGTAC TAATTCTTTT CATGTCACGG AGATAAATTT      3900

TGTTGCGCAA AATTATTTGG AAATTAACGT TGATTTCAAT TTCTTTTACT ACTAAACTAA      3960

TCACAATACG CGAAACTTTT TCTAGTTAAT TAATGGCATT AATGTTTATT TCCATACAGT      4020

AATTGCATAT TATGTTCACT TGATAGTCTA TGACCTAATT CCCGCCGACC ACAATTTAGT      4080

TATTTAGAAT TTCAACTTCT AAAGCAACAA TACTGTCTTC CACAAAGACT TTTACTATGA      4140

TATAACTACC GGTGTGTTGC GCCGAGCAAT TTTGCATAAT CAAAATTTTA GAATGTTCAA      4200
```

```
CGATTTTCTC GTGTTGCACC TTATTGAAAT AATTTTCTTA ATTTCTTTTT AGGTGTAGCA    4260

TATCATCGAC GTGTACATCA CTGTCCACTT GTATCAGTTA TATGTAATAT AAGTTTTAGT    4320

TTGCTTCTTG TACCAAATTA ATTACTATAA GTATTTAGAC TTGTTATATG TTTACCGAGT    4380

AAGTAACATC TATGTCTACT AAAACCACTT CATTATCTGT ACATATAATC GATTTTTGAT    4440

ATACGTTAGT GCTTTAATTT ACTATTTTAT GTCATTACAA TTTAAAACTG ATTTAAGTTC    4500

CCTAAATATA ATTTACGACT GGTTCATGAA TAGCAATTTA ATCGCTATGC CTTAGGCGCC    4560

TTAAG                                                                4565
```

(2) INFORMATION FOR SEQ ID NO: 3:

(i) SEQUENCE CHARACTERISTICS:
        (A) LENGTH: 800 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

```
Met Ser Glu Ile Ile Gln Asp Leu Ser Leu Glu Asp Val Leu Gly Asp
1               5                   10                  15

Arg Phe Gly Arg Tyr Ser Lys Tyr Ile Ile Gln Glu Arg Ala Leu Pro
                20                  25                  30

Asp Val Arg Asp Gly Leu Lys Pro Val Gln Arg Arg Ile Leu Tyr Ala
            35                  40                  45

Met Tyr Ser Ser Gly Asn Thr His Asp Lys Asn Phe Arg Lys Ser Ala
        50                  55                  60

Lys Thr Val Gly Asp Val Ile Gly Gln Tyr His Pro His Gly Asp Ser
65                  70                  75                  80

Ser Val Tyr Glu Ala Met Val Arg Leu Ser Gln Asp Trp Lys Leu Arg
                85                  90                  95

His Val Leu Ile Glu Met His Gly Asn Asn Gly Ser Ile Asp Asn Asp
                100                 105                 110

Pro Pro Ala Ala Met Arg Tyr Thr Glu Ala Lys Leu Ser Leu Leu Ala
            115                 120                 125

Glu Glu Leu Leu Arg Asp Ile Asn Lys Glu Thr Val Ser Phe Ile Pro
        130                 135                 140

Asn Tyr Asp Asp Thr Thr Leu Glu Pro Met Val Leu Pro Ser Arg Phe
145                 150                 155                 160

Pro Asn Leu Leu Val Asn Gly Ser Thr Gly Ile Ser Ala Gly Tyr Ala
                165                 170                 175

Thr Asp Ile Pro Pro His Asn Leu Ala Glu Val Ile Gln Ala Thr Leu
                180                 185                 190

Lys Tyr Ile Asp Asn Pro Asp Ile Thr Val Asn Gln Leu Met Lys Tyr
            195                 200                 205

Ile Lys Gly Pro Asp Phe Pro Thr Gly Gly Ile Ile Gln Gly Ile Asp
        210                 215                 220

Gly Ile Lys Lys Ala Tyr Glu Ser Gly Lys Gly Arg Ile Ile Val Arg
225                 230                 235                 240

Ser Lys Val Glu Glu Glu Thr Leu Arg Asn Gly Arg Lys Gln Leu Ile
                245                 250                 255

Ile Thr Glu Ile Pro Tyr Glu Val Asn Lys Gly Ser Leu Val Lys Arg
                260                 265                 270
```

-continued

```
Ile Asp Glu Leu Arg Ala Asp Lys Lys Val Asp Gly Ile Val Glu Val
            275                 280                 285

Arg Asp Glu Thr Asp Arg Thr Gly Leu Arg Ile Ala Ile Glu Leu Lys
            290                 295                 300

Lys Asp Val Asn Ser Glu Ser Ile Lys Asn Tyr Leu Tyr Lys Asn Ser
305                 310                 315                 320

Asp Leu Gln Ile Ser Tyr Asn Phe Asn Met Val Ala Ile Ser Asp Gly
                    325                 330                 335

Arg Pro Lys Leu Met Gly Ile Arg Gln Ile Ile Asp Ser Tyr Leu Asn
                340                 345                 350

His Gln Ile Glu Val Val Ala Asn Arg Thr Lys Phe Glu Leu Asp Asn
            355                 360                 365

Ala Glu Lys Arg Met His Ile Val Glu Gly Leu Ile Lys Ala Leu Ser
            370                 375                 380

Ile Leu Asp Lys Val Ile Glu Leu Ile Arg Ser Ser Lys Asn Lys Arg
385                 390                 395                 400

Asp Ala Lys Glu Asn Leu Ile Glu Val Tyr Glu Phe Thr Glu Glu Gln
                    405                 410                 415

Ala Glu Ala Ile Val Met Leu Gln Leu Tyr Arg Leu Thr Asn Thr Asp
                420                 425                 430

Ile Val Ala Leu Glu Gly Glu His Lys Glu Leu Glu Ala Leu Ile Lys
            435                 440                 445

Gln Leu Arg His Ile Leu Asp Asn His Asp Ala Leu Leu Asn Val Ile
450                 455                 460

Lys Glu Glu Leu Asn Glu Ile Lys Lys Phe Lys Ser Glu Arg Leu
465                 470                 475                 480

Ser Leu Ile Glu Ala Glu Ile Glu Ile Lys Ile Asp Lys Glu Val
                    485                 490                 495

Met Val Pro Ser Glu Glu Val Ile Leu Ser Met Thr Arg His Gly Tyr
                500                 505                 510

Ile Lys Arg Thr Ser Ile Arg Ser Phe Asn Ala Ser Gly Val Glu Asp
            515                 520                 525

Ile Gly Leu Lys Asp Gly Asp Ser Leu Leu Lys His Gln Glu Val Asn
            530                 535                 540

Thr Gln Asp Thr Val Leu Val Phe Thr Asn Lys Gly Arg Tyr Leu Phe
545                 550                 555                 560

Ile Pro Val His Lys Leu Arg Asp Ile Arg Trp Lys Glu Leu Gly Gln
                    565                 570                 575

His Val Ser Gln Ile Val Pro Ile Glu Glu Asp Glu Val Val Ile Asn
                580                 585                 590

Val Tyr Asn Glu Lys Asp Phe Asn Thr Asp Ala Phe Tyr Val Phe Ala
            595                 600                 605

Thr Gln Asn Gly Met Ile Lys Lys Ser Thr Val Pro Leu Phe Lys Thr
            610                 615                 620

Thr Arg Pro Asn Lys Pro Leu Ile Ala Thr Lys Val Lys Glu Asn Asp
625                 630                 635                 640

Asp Leu Ile Ser Val Met Arg Phe Glu Lys Asp Gln Leu Ile Thr Val
                    645                 650                 655

Ile Thr Asn Lys Gly Met Ser Leu Thr Tyr Asn Thr Ser Glu Leu Ser
                660                 665                 670

Asp Thr Gly Leu Arg Ala Ala Gly Val Lys Ser Ile Asn Leu Lys Val
            675                 680                 685

Glu Asp Phe Val Val Met Thr Glu Gly Val Ser Glu Asn Asp Thr Ile
```

```
                690              695               700
Leu Met Ala Thr Gln Arg Gly Ser Leu Lys Arg Ile Ser Phe Lys Ile
705                 710                 715                 720

Leu Gln Val Ala Lys Arg Ala Gln Arg Gly Ile Thr Leu Leu Lys Glu
                725                 730                 735

Leu Lys Lys Asn Pro His Arg Ile Val Ala Ala His Val Val Thr Gly
                740                 745                 750

Glu His Ser Gln Tyr Thr Leu Tyr Ser Lys Ser Asn Glu Glu His Gly
                755                 760                 765

Leu Ile Asn Asp Ile His Lys Ser Glu Gln Tyr Thr Asn Gly Ser Phe
770                 775                 780

Ile Val Asp Thr Asp Asp Phe Gly Glu Val Ile Asp Met Tyr Ile Ser
785                 790                 795                 800
```

(2) INFORMATION FOR SEQ ID NO: 4:

(i) SEQUENCE CHARACTERISTICS:
        (A) LENGTH: 2402 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

```
GTGAGTGAAA TAATTCAAGA TTTATCACTT GAAGATGTTT TAGGTGATCG CTTTGGAAGA      60
TATAGTAAAT ATATTATTCA AGAGCGTGCA TTGCCAGATG TTCGTGATGG TTTAAAACCA     120
GTACAACGTC GTATTTTATA CGCAATGTAT TCAAGTGGTA ATACACACGA TAAAAATTTC     180
CGTAAAAGTG CGAAAACAGT CGGTGATGTT ATTGGTCAAT ATCATCCACA TGGAGACTCC     240
TCAGTGTACG AAGCAATGGT CCGTTTAAGT CAAGACTGGA AGTTACGACA TGTCTTAATA     300
GAAATGCATG GTAATAATGG TAGTATCGAT AATGATCCGC CAGCGGCAAT GCGTTACACT     360
GAAGCTAAGT TAAGCTTACT AGCTGAAGAG TTATTACGTG ATATTAATAA AGAGACAGTT     420
TCTTTCATTC CAAACTATGA TGATACGACA CTCGAACCAA TGGTATTGCC ATCAAGATTT     480
CCTAACTTAC TAGTGAATGG TTCTACAGGT ATATCTGCAG GTTACGCGAC AGATATACCA     540
CCACTAATTT AGCTGAAGTG ATTCAAGCAA CACTTAAATA TATTGATAAT CCGGATATTA     600
TAGTCAATCA ATTAATGAAA TATATTAAAG GTCCTGATTT TCCAACTGGT GGTATTATTC     660
AAGGTATTGA TGGTATTAAA AAAGCTTATG AATCAGGTAA AGGTAGAATT ATAGTTCGTT     720
CTAAAGTTGA AGAAGAAATT TTACGCAATG GACGTAAACA GTTAATTATT ACTGAAATTC     780
CATATGAAGT GAACAAAGGT AGCTTAGTAA ACGTATCGA TGAATTACGT GCTGACAAAA     840
AAGTCGATGG TATCGTTGAA GTACGTGATG AAACTGATAG AACTGGTTTA CGAATAGCAA     900
TTGAATTGAA AAAAGATGTG AACAGTGAAT CAATCAAAAA TTATCTTTAT AAAAACTCTG     960
ATTTACAGAT TCATATAAT TTCAACATGG TCGCTATTAG TGATGGTCGT CCAAAATTGA    1020
TGGGTATTCG TCAAATTATA GATAGTTATT TGAATCATCA AATTGAGGTT GTTGCAAATA    1080
GAACGAAGTT TGAATTAGAT AATGCTGAAA ACGTATGCA TATCGTTGAA GGTTTGATTA    1140
AAGCGTTGTC AATTTTAGAT AAAGTAATCG AATTGATTCG TAGCTCTAAA ACAAGCGTG    1200
ACGCTAAAGA AAACCTTATC GAAGTATACG AGTTCACAGA GAACAGGCT GAAGCAATTG    1260
TAATGTTACA GTTATATCGT TTAACAAACA CTGACATAGT TGCGCTTGAA GGTGAACATA    1320
AGAACTTGA AGCATTAATC AAACAATTAC GTCATATTCT TGATAACCAT GATGCATTAT    1380
```

-continued

```
TGAATGTCAT AAAAGAAGAA TTGAATGAAA TTAAAAAGAA ATTCAAATCT GAACGACTGT      1440

CTTTAATTGA AGCAGAAATT GAAGAAATTA AAATTGACAA AGAAGTTATG GTGCCTAGTG      1500

AAGAAGTTAT TTTAAGTATG ACACGTCATG GATATATTAA ACGTACTTCT ATTCGTAGCT      1560

TTAATGCTAG CGGTGTTGAA GATATTGGTT TAAAAGATGG TGACAGTTTA CTTAAACATC      1620

AAGAAGTAAA TACGCAAGAT ACCGTACTAG TATTTACAAA TAAAGGTCGT TATCTATTTA      1680

TACCAGTTCA TAAATTACGA GATATTCGTT GGAAAGAATT GGGGCAACAT GTATCACAAA      1740

TAGTTCCTAT CGAAGAAGAT GAAGTGGTTA TTAATGTTTA TAATGAAAAG GACTTTAATA      1800

CTGATGCATT TTATGTTTTT GCGACTCAAA ATGGCATGAT TAAGAAAAGT ATAGTGCCTC      1860

TATTTAAAAC AACGCGTTTT AATAAACCTT TAATTGCAAC TAAAGTTAAA GAAAATGATG      1920

ATTTGATTAG TGTTATGCGT TTTGAAAAAG ATCAATTAAT TACCGTAATT ACAAATAAAG      1980

GTATGTCATT AACGTATAAT ACAAGTGAAC TATCAGATAC TGGATTAAGG GCGGCTGGTG      2040

TTAAATCAAT AAATCTTAAA GTTGAAGATT TCGTTGTTAT GACAGAAGGT GTTTCTGAAA      2100

ATGATACTAT ATTGATGGCC ACACAACGCG GCTCGTTAAA ACGTATTAGT TTTAAAATCT      2160

TACAAGTTGC TAAAAGAGCA CAACGTGGAA TAACTTTATT AAAAGAATTA AAGAAAAATC      2220

CACATCGTAT AGTAGCTGCA CATGTAGTGA CAGGTGAACA TAGTCAATAT ACATTATATT      2280

CAAAATCAAA CGAAGAACAT GGTTTAATTA ATGATATTCA TAAATCTGAA CAATATACAA      2340

ATGGCTCATT CATTGTAGAT ACAGATGATT TTGGTGAAGT AATAGACATG TATATTAGCT      2400

AA                                                                    2402
```

(2) INFORMATION FOR SEQ ID NO: 5:

(i) SEQUENCE CHARACTERISTICS:
        (A) LENGTH: 663 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

```
Met Asn Lys Gln Asn Asn Tyr Ser Asp Asp Ser Ile Gln Val Leu Glu
1               5                   10                  15

Gly Leu Glu Ala Val Arg Lys Arg Pro Gly Met Tyr Ile Gly Ser Thr
            20                  25                  30

Asp Lys Arg Gly Leu His His Leu Val Tyr Glu Ile Val Asp Asn Ser
        35                  40                  45

Val Asp Glu Val Leu Asn Gly Tyr Gly Asn Glu Ile Asp Val Thr Ile
    50                  55                  60

Asn Lys Asp Gly Ser Ile Ser Ile Glu Asp Asn Gly Arg Gly Met Pro
65                  70                  75                  80

Thr Gly Ile His Lys Ser Gly Lys Pro Thr Val Glu Val Ile Phe Thr
                85                  90                  95

Val Leu His Ala Gly Gly Lys Phe Gly Gln Gly Tyr Lys Thr Ser
            100                 105                 110

Gly Gly Leu His Gly Val Gly Ala Ser Val Val Asn Ala Leu Ser Glu
        115                 120                 125

Trp Leu Glu Val Glu Ile His Arg Asp Gly Asn Ile Tyr His Gln Ser
    130                 135                 140

Phe Lys Asn Gly Gly Ser Pro Ser Ser Gly Leu Val Lys Lys Gly Lys
145                 150                 155                 160
```

-continued

```
Thr Lys Lys Thr Gly Thr Lys Val Thr Phe Lys Pro Asp Asp Thr Ile
                165                 170                 175
Phe Lys Ala Ser Thr Ser Phe Asn Phe Asp Val Leu Ser Glu Arg Leu
            180                 185                 190
Gln Glu Ser Ala Phe Leu Leu Lys Asn Leu Lys Ile Thr Leu Asn Asp
        195                 200                 205
Leu Arg Ser Gly Lys Glu Arg Gln Glu His Tyr His Tyr Glu Glu Gly
    210                 215                 220
Ile Lys Glu Phe Val Ser Tyr Val Asn Glu Gly Lys Glu Val Leu His
225                 230                 235                 240
Asp Val Ala Thr Phe Ser Gly Glu Ala Asn Gly Ile Glu Val Asp Val
            245                 250                 255
Ala Phe Gln Tyr Asn Asp Gln Tyr Ser Glu Ser Ile Leu Ser Phe Val
        260                 265                 270
Asn Asn Val Arg Thr Lys Asp Gly Gly Thr His Glu Val Gly Phe Lys
    275                 280                 285
Thr Ala Met Thr Arg Val Phe Asn Asp Tyr Ala Arg Arg Ile Asn Glu
290                 295                 300
Leu Lys Thr Lys Asp Lys Asn Leu Asp Gly Asn Asp Ile Arg Glu Gly
305                 310                 315                 320
Leu Thr Ala Val Val Ser Val Arg Ile Pro Glu Glu Leu Leu Gln Phe
            325                 330                 335
Glu Gly Gln Thr Lys Ser Lys Leu Gly Thr Ser Glu Ala Arg Ser Ala
        340                 345                 350
Val Asp Ser Val Val Ala Asp Lys Leu Pro Phe Tyr Leu Glu Glu Lys
    355                 360                 365
Gly Gln Leu Ser Lys Ser Leu Val Lys Lys Ala Ile Lys Ala Gln Gln
    370                 375                 380
Ala Arg Glu Ala Ala Arg Lys Ala Arg Glu Asp Ala Arg Ser Gly Lys
385                 390                 395                 400
Lys Asn Lys Arg Lys Asp Thr Leu Leu Ser Gly Lys Leu Thr Pro Ala
                405                 410                 415
Gln Ser Lys Asn Thr Glu Lys Asn Glu Leu Tyr Leu Val Glu Gly Asp
            420                 425                 430
Ser Ala Gly Gly Ser Ala Lys Leu Gly Arg Asp Arg Lys Phe Gln Ala
        435                 440                 445
Ile Leu Pro Leu Arg Gly Lys Val Ile Asn Thr Glu Lys Ala Arg Leu
    450                 455                 460
Glu Asp Ile Phe Lys Asn Glu Glu Ile Asn Thr Ile His Thr Ile
465                 470                 475                 480
Gly Ala Gly Val Gly Thr Asp Phe Lys Ile Glu Asp Ser Asn Tyr Asn
                485                 490                 495
Arg Val Ile Ile Met Thr Asp Ala Asp Thr Asp Gly Ala His Ile Gln
            500                 505                 510
Val Leu Leu Leu Thr Phe Phe Lys Tyr Met Lys Pro Leu Val Gln
        515                 520                 525
Ala Gly Arg Val Phe Ile Ala Leu Pro Pro Leu Tyr Lys Leu Glu Lys
    530                 535                 540
Gly Lys Gly Lys Thr Lys Arg Val Glu Tyr Ala Trp Thr Asp Glu Glu
545                 550                 555                 560
Leu Asn Lys Leu Gln Lys Glu Leu Gly Lys Gly Phe Thr Leu Gln Arg
                565                 570                 575
Tyr Lys Gly Leu Gly Glu Met Asn Pro Glu Gln Leu Trp Glu Thr Thr
```

```
                580              585              590
Met Asn Pro Glu Thr Arg Thr Leu Ile Arg Val Gln Val Glu Asp Glu
                    595              600              605
Val Arg Ser Ser Lys Arg Val Thr Thr Leu Met Gly Asp Lys Val Gln
        610              615              620
Pro Arg Arg Glu Trp Ile Glu Lys His Val Glu Phe Gly Met Gln Glu
625              630              635              640
Asp Gln Ser Ile Leu Asp Asn Ser Glu Val Gln Val Leu Glu Asn Asp
                645              650              655
Gln Phe Asp Glu Glu Ile
                660
```

(2) INFORMATION FOR SEQ ID NO: 6:

(i) SEQUENCE CHARACTERISTICS:
        (A) LENGTH: 1992 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

```
ATGAATAAAC AAAATAATTA TTCAGATGAT TCAATACAGG TTTTAGAGGG GTTAGAAGCA      60
GTTCGTAAAA GACCTGGTAT GTATATTGGA TCAACTGATA AACGGGGATT ACATCATCTA     120
GTATATGAAA TTGTCGATAA CTCCGTCGAT GAAGTATTGA ATGGTTACGG TAACGAAATA     180
GATGTAACAA TTAATAAAGA TGGTAGTATT TCTATAGAAG ATAATGGACG TGGTATGCCA     240
ACAGGTATAC ATAAATCAGG TAAACCGACA GTCGAAGTTA TCTTTACTGT TTTACATGCA     300
GGAGGTAAAT TTGGACAAGG TGGCTATAAA ACTTCAGGTG GTCTTCACGG CGTTGGTGCT     360
TCAGTGGTAA ATGCATTGAG TGAATGGCTT GAAGTTGAAA TCCATCGAGA TGGTAATATA     420
TATCATCAAA GTTTTAAAAA CGGTGGTTCG CCATCTTCAG GTTTAGTGAA AAAAGGTAAA     480
ACTAAGAAAA CAGGTACCAA AGTAACATTT AAACCTGATG ACACAATTTT TAAAGCATCT     540
ACATCATTTA ATTTTGATGT TTTAAGTGAA CGACTACAAG AGTCTGCGTT CTTATTGAAA     600
AATTTAAAAA TAACGCTTAA TGATTTACGC AGTGGTAAAG AGCGTCAAGA GCATTACCAT     660
TATGAAGAAG GAATCAAAGA GTTTGTTAGT TATGTCAATG AAGGAAAAGA AGTTTTGCAT     720
GACGTGGCTA CATTTTCAGG TGAAGCAAAT GGTATAGAGG TAGACGTAGC TTTCCAATAT     780
AATGATCAAT ATTCAGAAAG TATTTTAAGT TTTGTAAATA ATGTACGTAC TAAAGATGGT     840
GGTACACATG AAGTTGGTTT TAAAACAGCA ATGACACGCG TATTTAATGA TTATGCACGT     900
CGTATTAATG AACTTAAAAC AAAAGATAAA AACTTAGATG GTAATGATAT TCGTGAAGGT     960
TTAACAGCTG TTGTGTCTGT TCGTATTCCA GAAGAATTAT TGCAATTTGA AGGACAAACG    1020
AAATCTAAAT TGGGTACTTC TGAAGCTAGA AGTGCTGTTG ATTCAGTTGT TGCAGACAAA    1080
TTGCCATTCT ATTTAGAAGA AAAAGGACAA TTGTCTAAAT CACTTGTGAA AAAAGCGATT    1140
AAAGCACAAC AAGCAAGGGA AGCTGCACGT AAAGCTCGTG AAGATGCTCG TTCAGGTAAG    1200
AAAAACAAGC GTAAAGACAC TTTGCTATCT GGTAAATTAA CACCTGCACA AGTAAAAAAC    1260
ACTGAAAAAA ATGAATTGTA TTTAGTCGAA GGTGATTCTG CGGGAGGTTC AGCAAAACTT    1320
GGACGAGACC GCAAATTCCA AGCGATATTA CCATTACGTG GTAAGGTAAT TAATACAGAG    1380
AAAGCACGTC TAGAAGATAT TTTTAAAAAT GAAGAAATTA ATACAATTAT CCACACAATC    1440
GGGGCAGGCG TTGGTACTGA CTTTAAAATT GAAGATAGTA ATTATAATCG TGTAATTATT    1500
```

```
ATGACTGATG CTGATACTGA TGGTGCGCAT ATTCAAGTGC TATTGTTAAC ATTCTTCTTC      1560

AAATATATGA AACCGCTTGT TCAAGCAGGT CGTGTATTTA TTGCTTTACC TCCACTTTAT      1620

AAATTGGAAA AAGGTAAAGG CAAAACAAAG CGAGTTGAAT ACGCTTGGAC AGACGAAGAG      1680

CTTAATAAAT TGCAAAAAGA ACTTGGTAAA GGCTTCACGT TACAACGTTA CAAAGGTTTG      1740

GGTGAAATGA ACCCTGAACA ATTATGGGAA ACGACGATGA ACCCAGAAAC ACGAACTTTA      1800

ATTCGTGTAC AAGTTGAAGA TGAAGTGCGT TCATCTAAAC GTGTAACAAC ATTAATGGGT      1860

GACAAAGTAC AACCTAGACG TGAATGGATT GAAAAGCATG TTGAGTTTGG TATGCAAGAG      1920

GACCAAAGTA TTTTAGATAA TTCTGAAGTA CAAGTGCTTG AAAATGATCA ATTTGATGAG      1980

GAGGAAATCT AG                                                          1992

(2) INFORMATION FOR SEQ ID NO: 7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

GCGCGAATTC GATGGWYTWA AACCWGTWCA                                       30

(2) INFORMATION FOR SEQ ID NO: 8:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

CGCGAAGCTT TTCWGTATAW CKCATWGCWG C                                     31

(2) INFORMATION FOR SEQ ID NO: 9:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

GCGCGAATTC TWCATGCWGG WGGWAAATT                                        29

(2) INFORMATION FOR SEQ ID NO: 10:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

CGCGAAGCTT WCCWCCWGCW GAATCWCCTT C                                     31
```

(2) INFORMATION FOR SEQ ID NO: 11:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 11:

```
Ala Ala Met Arg Tyr Thr Glu
 1               5
```

(2) INFORMATION FOR SEQ ID NO: 12:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 12:

```
Tyr His Pro His Gly Asp Ser
 1               5
```

(2) INFORMATION FOR SEQ ID NO: 13:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

GGCGGATCCC ATATGGCTGA ATTACCTCA                                   29

(2) INFORMATION FOR SEQ ID NO: 14:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 14:

GGCGGAATTC GACGGCTCTC TTTCATTAC                                   29

(2) INFORMATION FOR SEQ ID NO: 15:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 15:

GGCCGGATCC CATATGAGTG AAATAATTCA AGATT                            35

(2) INFORMATION FOR SEQ ID NO: 16:

```
        (i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 16:

GGCCGAATTC TAATAATTAA CTGTTTACGT CC                                  32

(2) INFORMATION FOR SEQ ID NO: 17:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 17:

GGCCGAGCTC CAATTCTTCT TTTATGACAT TC                                  32
```